United States Patent
Cunningham et al.

(10) Patent No.: US 8,986,229 B2
(45) Date of Patent: Mar. 24, 2015

(54) TONGUE STRENGTH EVALUATION SYSTEM AND METHOD

(71) Applicant: CCB Research Group LLC, Lexington, KY (US)

(72) Inventors: Thomas J. Cunningham, Atlanta, GA (US); Gilson J. Capilouto, Lexington, KY (US); Timothy A. Butterfield, Lexington, KY (US)

(73) Assignee: CCB Research Group, LLC., Lexington, KY (US)

( * ) Notice: Subject to any disclaimer, the term of this patent is extended or adjusted under 35 U.S.C. 154(b) by 0 days.

(21) Appl. No.: 14/166,281

(22) Filed: Jan. 28, 2014

(65) Prior Publication Data

US 2014/0142415 A1    May 22, 2014

Related U.S. Application Data

(62) Division of application No. 13/479,640, filed on May 24, 2012, now Pat. No. 8,663,131.

(60) Provisional application No. 61/490,892, filed on May 27, 2011, provisional application No. 61/578,004, filed on Dec. 20, 2011.

(51) Int. Cl.
*A61B 5/103* (2006.01)
*A61B 5/00* (2006.01)
*A61B 5/03* (2006.01)
*A61B 5/22* (2006.01)
*A61J 17/00* (2006.01)

(52) U.S. Cl.
CPC ............. *A61B 5/4552* (2013.01); *A61B 5/038* (2013.01); *A61B 5/228* (2013.01); *A61B 5/682* (2013.01); *A61J 17/00* (2013.01); *A61B 2560/0462* (2013.01); *A61B 2562/0247* (2013.01); *A61B 2562/0261* (2013.01)
USPC ............................................ 600/590; 600/587

(58) Field of Classification Search
CPC ..... A61B 5/228; A61B 5/4547; A61C 19/045
USPC .................................................. 600/587, 590
See application file for complete search history.

(56) References Cited

U.S. PATENT DOCUMENTS

| | | | | |
|---|---|---|---|---|
| 3,417,743 A | * | 12/1968 | Carrera ......................... | 600/591 |
| 3,790,016 A | * | 2/1974 | Kron ............................ | 215/11.1 |
| 4,232,687 A | * | 11/1980 | Anderson-Shanklin ...... | 600/590 |
| 4,488,873 A | * | 12/1984 | Bloomfield et al. ........... | 433/71 |

(Continued)

*Primary Examiner* — Sean Dougherty
*Assistant Examiner* — Daniel Cerioni
(74) *Attorney, Agent, or Firm* — Quinn Law Group, PLLC.

(57) ABSTRACT

An apparatus for evaluating the tongue strength of a subject during a sucking event includes an insert positioned within a nipple element to provide an output in response to deformation of the nipple element during a sucking event. The output is at least one of resistive force exerted against the subject's tongue and movement measurement of deformation force exerted on the nipple element during the sucking event. The apparatus is configurable to evaluate nutritive sucking (NS) or non-nutritive sucking (NNS) capabilities of the subject. The insert may be a sensing device, a compliance element, an intermediate device or a combination of these. A coupling device is configured to position the insert relative to the nipple element and/or to receive output from the insert. A method includes evaluating tongue strength of a subject during NS or NNS and using inserts providing increasing levels of resistive force to exercise the subject's tongue.

34 Claims, 9 Drawing Sheets

(56) References Cited

U.S. PATENT DOCUMENTS

| | | | | |
|---|---|---|---|---|
| 4,629,424 A | * | 12/1986 | Lauks et al. | 433/6 |
| 4,697,601 A | * | 10/1987 | Durkee et al. | 600/590 |
| 5,119,831 A | * | 6/1992 | Robin et al. | 600/587 |
| 5,452,727 A | * | 9/1995 | Tura et al. | 600/590 |
| 5,830,235 A | * | 11/1998 | Standley | 606/234 |
| 5,853,005 A | * | 12/1998 | Scanlon | 600/459 |
| 6,033,367 A | * | 3/2000 | Goldfield | 600/529 |
| 6,109,100 A | * | 8/2000 | Buckley et al. | 73/198 |
| 6,702,765 B2 | * | 3/2004 | Robbins et al. | 600/590 |
| 7,333,020 B2 | * | 2/2008 | Cohen et al. | 340/573.1 |
| 8,427,178 B2 | * | 4/2013 | Gianetti | 324/679 |
| 2006/0074354 A1 | * | 4/2006 | Barlow et al. | 600/590 |
| 2006/0079814 A1 | * | 4/2006 | Barlow et al. | 600/590 |
| 2008/0077183 A1 | * | 3/2008 | Cohen | 606/234 |
| 2008/0183107 A1 | * | 7/2008 | Miller et al. | 600/590 |
| 2009/0156967 A1 | * | 6/2009 | Cohen | 600/590 |
| 2009/0157477 A1 | * | 6/2009 | Cohen | 705/10 |
| 2010/0121224 A1 | * | 5/2010 | Toyota et al. | 600/590 |
| 2010/0222706 A1 | * | 9/2010 | Miyahara et al. | 600/590 |
| 2011/0054938 A1 | * | 3/2011 | Hood et al. | 705/3 |
| 2011/0172565 A1 | * | 7/2011 | Shih et al. | 600/587 |
| 2011/0190666 A1 | * | 8/2011 | Friedland et al. | 600/590 |
| 2011/0245850 A1 | * | 10/2011 | van der Burg et al. | 606/145 |

* cited by examiner

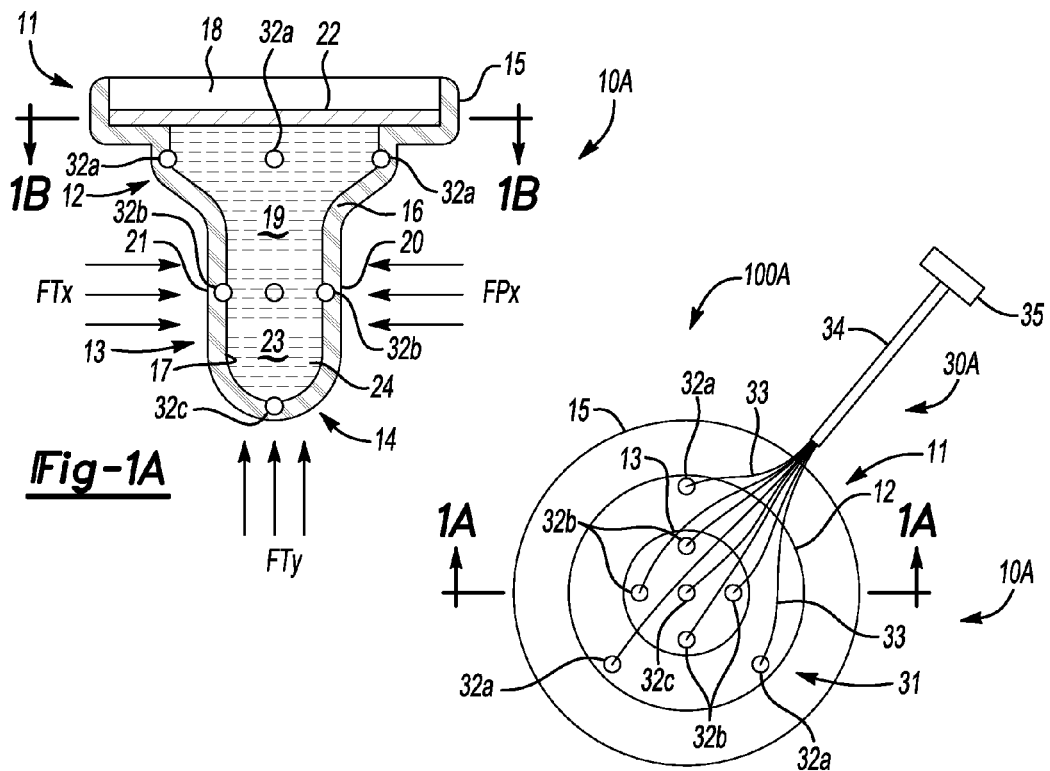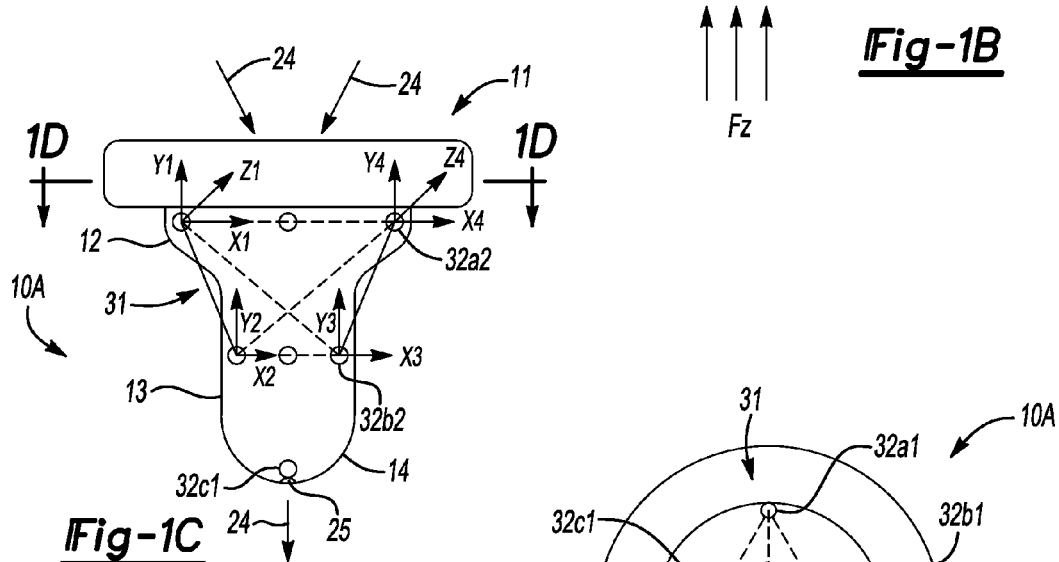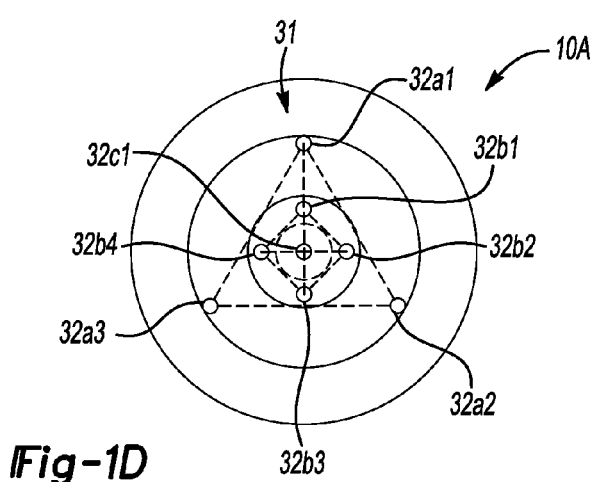

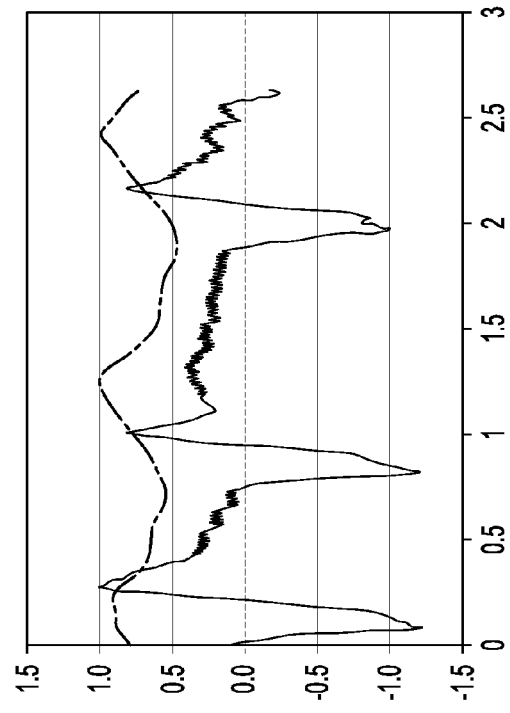
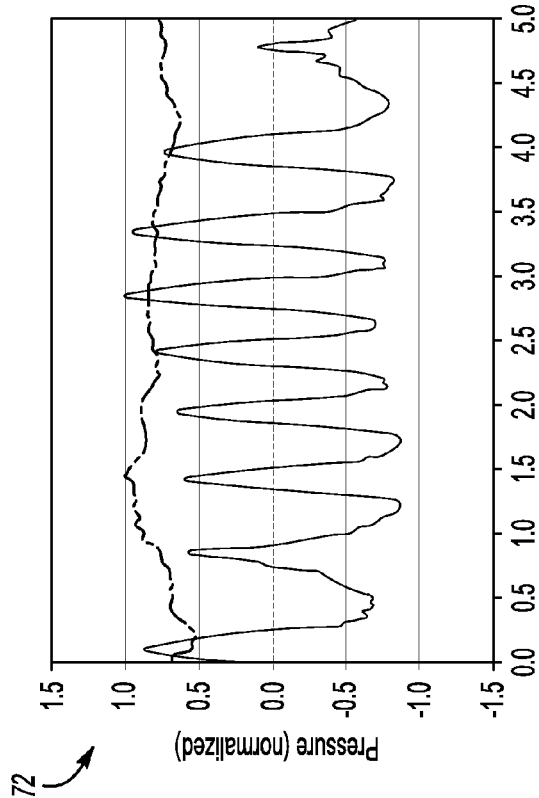

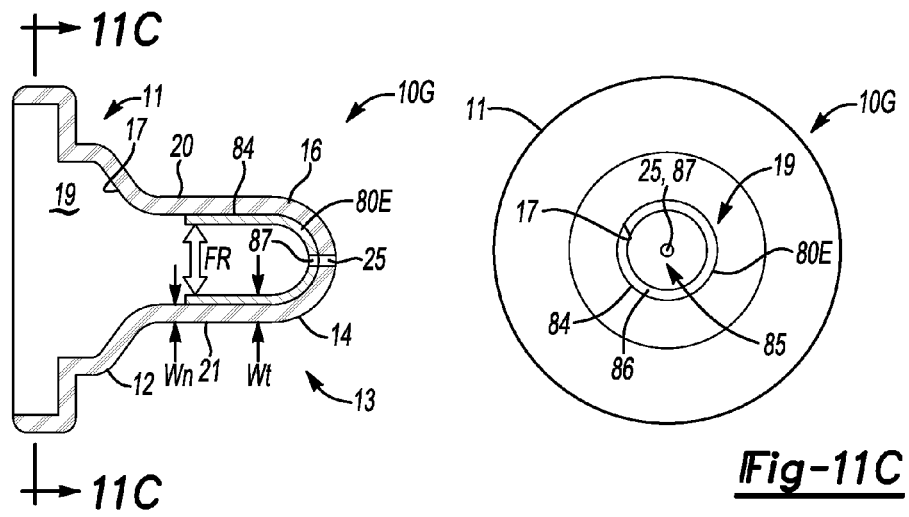
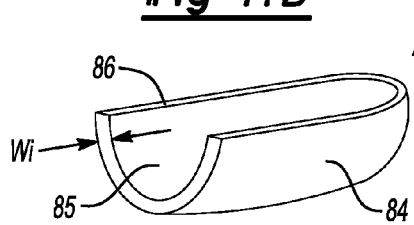
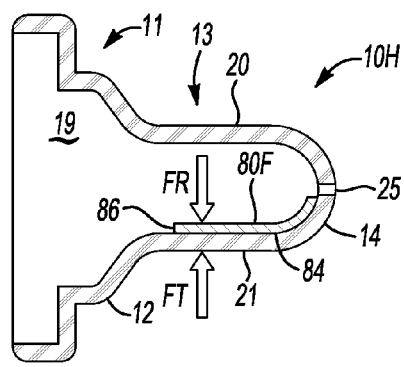
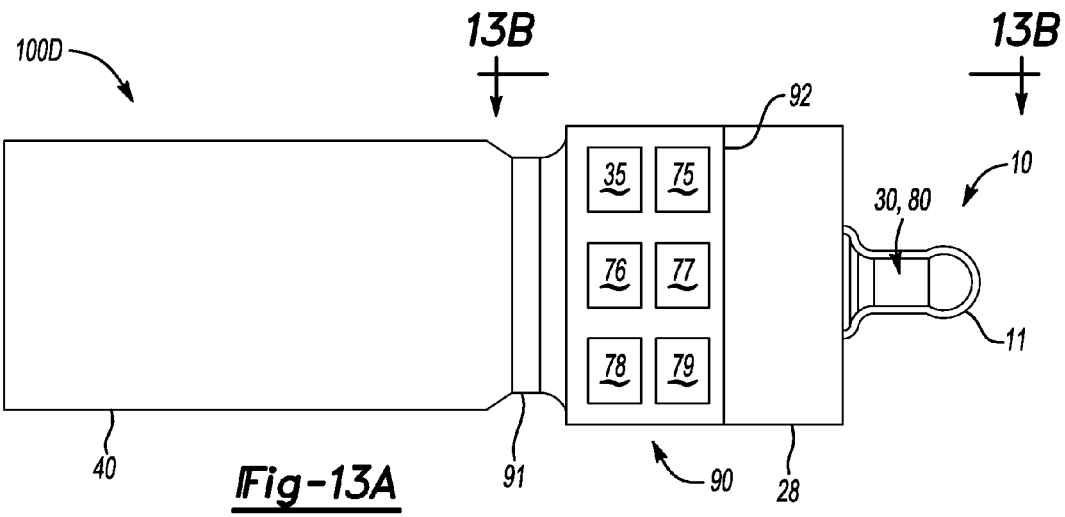

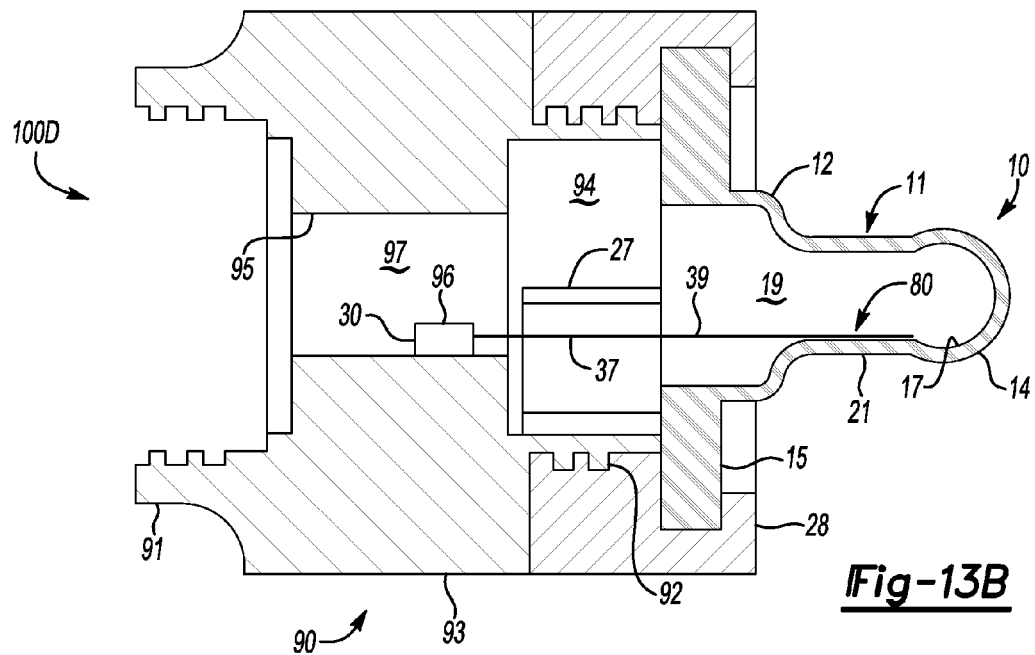
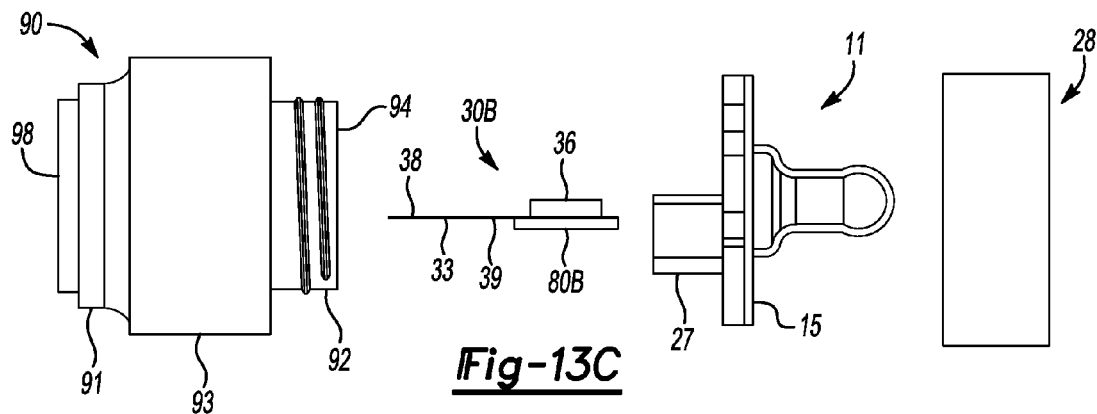
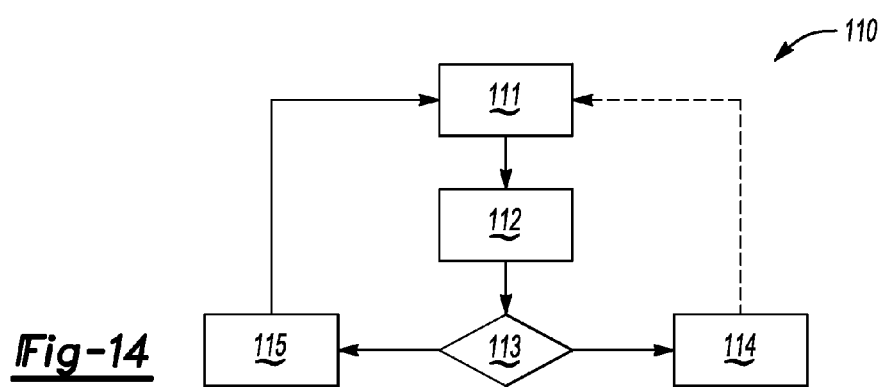

TONGUE STRENGTH EVALUATION SYSTEM AND METHOD

CROSS-REFERENCE TO RELATED APPLICATIONS

This application claims the benefit of U.S. Non-provisional application Ser. No. 13/479,640 filed May 24, 2012, U.S. Provisional Application 61/490,892 filed May 27, 2011, and U.S. Provisional Application 61/578,004 filed Dec. 20, 2011, which are each hereby incorporated by reference in their entirety.

TECHNICAL FIELD

The present disclosure relates to the field of biomechanics and more specifically to the evaluation of tongue movement and strength.

BACKGROUND

Measuring the movement and strength of an infant tongue during sucking on the nipple of a bottle or pacifier presents several challenges including, for example, the limited oral space of the infant available for direct measurement and alteration of motor control feedback mechanisms induced at the tongue interface, the limited amount of space available for instrumentation of the nipple, alterations required for instrumentation of the nipple which could affect natural feeding patterns, and obtaining accurate and precise measurements of tongue contact with the nipple interface. There are two stages of feeding where the tongue is applied to the nipple. During one stage, compression (squeezing) of the nipple by forces exerted on the nipple by the tongue compresses the nipple against the palate. In a nutritive sucking condition, a volume of fluid present in the nipple is pushed out of the nipple and into the oral cavity due to compression of the nipple. In the other stage, with the oral cavity sealed, the jaw and tongue drop down and away from the palate, enlarging the oral cavity and creating negative intra-oral suction. In a nutritive sucking condition, fluid is drawn (sucked) out of the nipple. Both stages are essential to infant feeding.

Adaptations to tongue muscle including decline of or lack of improvement in tongue strength may occur in premature infants who are artificially fed for a period of time. Using animal models, researchers have documented significant negative changes in tongue muscle responsiveness as a result of artificial feeding of newborn rats, which result in long term difficulties with feeding. As many as forty percent of premature infants exhibit both immature and atypical feeding patterns and those requiring prolonged respiratory support and those experiencing delayed oral feeding are most often affected. Because artificial feeding of premature infants may not be avoidable, determining whether tongue force is adequate for safe, efficient oral feeding, and developing interventions that lessen or eliminate any negative impact on the tongue muscle, such as interventions for strengthening the tongue during non-nutritive suck (NNS) and nutritive suck (NS), are necessary. Clinical use of NNS with preterm infants to promote oral feeding is well documented. Indications are that NNS intervention has a positive impact on transition from tube feedings to oral feedings, improves bottle feeding performance and decreases length of stay. Volume intake, number of tube feedings prior to reaching full oral feeds, and impact on growth and weight gain are outcomes that have not been positively associated with NNS, and the impact of NNS on other important oral feeding outcomes is not clear. Current measurement and evaluation methods are lacking and those that currently exist are subjective in nature and provide limited empirical evidence relative to assessment of infant feeding and swallowing.

SUMMARY

A system, method and apparatus to noninvasively evaluate the tongue movement and strength of a subject is provided. Measurements of tongue movement may be used to determine tongue strength parameters of an infant subject, including tongue force applied to a nipple during non-nutritive suck (NNS) and nutritive suck (NS). An intervention method directed at increasing NS tongue strength as well as NNS tongue strength of a subject with the intended outcome of positively impacting transition from tube feedings to oral feedings by improving bottle feeding performance of the subject is provided. The system, method and apparatus are configured to obtain direct measurement of the force of the tongue on the nipple interface in a noninvasive manner and to evaluate kinematic changes to the nipple during NNS and NS measurement by measuring tongue movement. The magnitude and direction of forces applied by the tongue to the nipple can be calculated through a calibration process of the evaluation apparatus and kinematic analysis of the applied forces such that measurements of tongue strength, work, impulse, and power or other derivations of force and time may be calculated from movement measurements obtained using the evaluation apparatus described herein.

An apparatus for evaluating the movement of the tongue of a subject is provided. Movement measurements obtained using the apparatus may be used to calculate tongue force and derive tongue strength parameters. The evaluation apparatus includes an insert configured to be positioned within a nipple element and to provide an output in response to deformation of the nipple element by a deformation force exerted on the nipple element during a sucking event. The output may be a resistive force exerted by the insert against the tongue of the subject during the sucking event, a movement measurement of the deformation force exerted on the nipple element during the sucking event, or a combination of these. The resistive force may be known or determined by calibration. The movement measurement output may be calibrated to the deformation or deformation force. The sucking event may be a nutritive sucking event wherein a fluid may be provided to the subject via the nipple element and the fluid may be in contact with the insert during the nutritive sucking event such that the nutritive sucking (NS) capability of the subject may be evaluated. The evaluation apparatus may be configured for non-nutritive sucking such that the non-nutritive sucking (NNS) capability of the subject may be evaluated.

The insert may be configured as a sensing device to provide an output which is a movement measurement of the deformation force exerted on the nipple element during the sucking event. The insert may be configured as a compliance element to provide an output which is a resistive force exerted in opposition to the deformation force and/or against the tongue of the subject during the sucking event. The insert may be configured to include a compliance element in communication with a sensing device, and may include an intermediate device in communication with one of the insert and the nipple element.

The evaluation apparatus may include a coupling device configured to be operatively connected to the nipple element, and to position the insert relative to the nipple element, and/or receive the movement measurement output provided by the insert. The coupling device may be configured to process the movement measurement by storing, displaying, analyzing and/or transmitting the output or a strength parameter determined from the movement measurement output. The coupling device may be configured to be sealably attached to a container to provide a sealed chamber in fluid communication with the nipple element. The sealed container may contain a liquid in fluid communication with the nipple element such that the insert is in contact with the liquid during the sucking event, and/or the sucking event may be a nutritive sucking event.

A system for evaluating the strength of the tongue of a subject during a sucking event is provided. The system includes the evaluation apparatus in selective communication with one or more devices configured as one or more of a data collector/analyzer, a transducer, a processor and a memory. The system may further include a calibration apparatus configured to calibrate the evaluation apparatus to provide a calibration of the output to the deformation of the nipple element. The evaluation apparatus may include a sealed chamber in fluid communication with the nipple element and a pressure gauge such that a change in pressure in the sealed container in response to deformation of the nipple element may be measured.

A method for evaluating the strength of the tongue of a subject is provided. The method includes providing an evaluation apparatus including an initial insert to a subject, conducting an initial sucking session with the subject using the evaluation apparatus including the initial insert characterized by a first resistive force, and evaluating the tongue strength of the subject using the output of the initial sucking session to determine if a strength objective or threshold established for the subject has been met. If the strength objection is not met, the method may further include providing the evaluation apparatus including a subsequent insert characterized by a subsequent resistive force which is different than the first resistive force, conducting a subsequent sucking session with the subject using the evaluation apparatus including the subsequent insert, and evaluating the tongue strength of the subject using the output of the subsequent sucking session to determine if a strength objective established for the subject has been met. The subsequent insert may be configured to exert a higher resistive force than the initial insert, to exercise the subject's tongue during the sucking event(s) to strengthen the tongue until the subject's sucking performance meets the threshold level or objective set for the subject. The method may include evaluation of the subject's nutritive and/or non-nutritive sucking capabilities.

The above features and advantages and other features and advantages of the present invention are readily apparent from the following detailed description of the best modes for carrying out the invention when taken in connection with the accompanying drawings.

BRIEF DESCRIPTION OF THE DRAWINGS

FIG. 1A is a schematic cross-sectional view of an instrumented nipple including an insert configured as a first example of a sensing device;

FIG. 1B is a schematic bottom view of the instrumented nipple of FIG. 1A;

FIG. 1C is a schematic side view of the instrumented nipple of FIG. 1A;

FIG. 1D is a schematic bottom view of the instrumented nipple of FIG. 1A showing the sensor array of the sensing device of FIGS. 1A-1C;

FIG. 4A is schematic illustration of example data provided by the tongue movement evaluation apparatus of FIG. 1D;

FIG. 4B is schematic illustration of example data provided by the tongue movement evaluation system of FIG. 3A using an evaluation apparatus configured for non-nutritive sucking (NNS);

FIG. 4C is schematic illustration of example data provided by the tongue movement evaluation system of FIG. 3A using an evaluation apparatus configured for nutritive sucking (NS);

FIG. 11B is a schematic cross-sectional illustration of an instrumented nipple including the compliance element of FIG. 11A;

FIG. 11C is an end view of the instrumented nipple of FIG. 11B;

FIG. 12A is a schematic perspective illustration of another example of a compliance element;

FIG. 12B is a schematic cross-sectional illustration of an instrumented nipple including the compliance element of FIG. 12A;

FIG. 13A is a schematic illustration of a tongue movement evaluation apparatus including a coupling device;

FIG. 13B is a schematic cross-sectional illustration of the tongue movement evaluation apparatus of FIG. 13A including the coupling device;

FIG. 13C is a schematic exploded view of the tongue movement evaluation apparatus of FIG. 13A including the coupling device; and FIG. 14 is a schematic flow diagram of a process for evaluating the tongue movement and/or tongue strength of a subject.

DETAILED DESCRIPTION

Figure 2A:
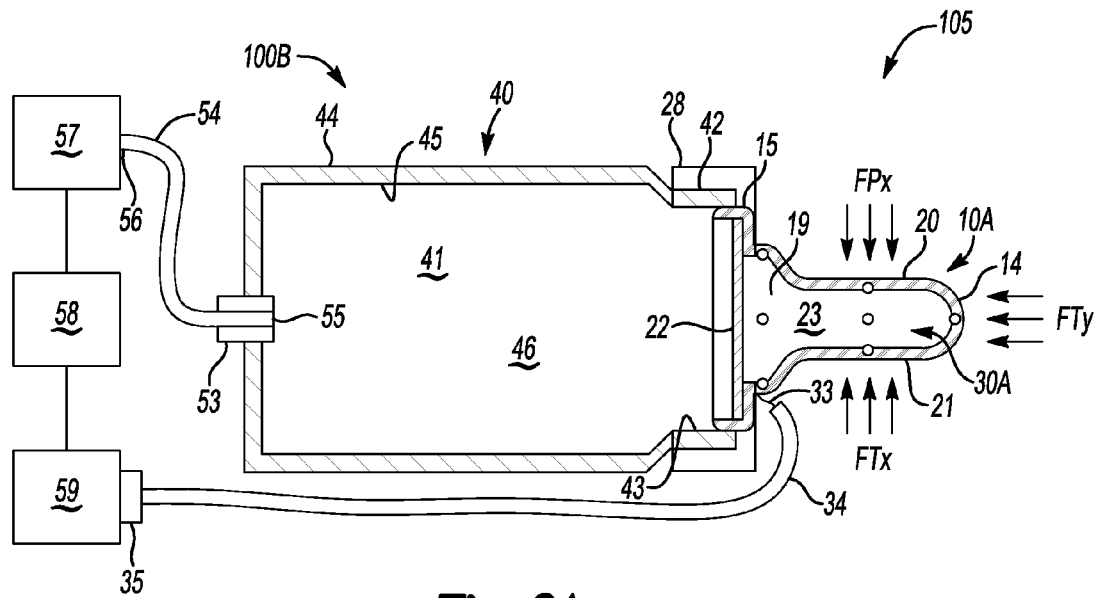
FIG. 2A is a schematic illustration of a tongue movement evaluation system including a cross-sectional view of a first example of a tongue movement evaluation apparatus.

A system, method and apparatus for noninvasive evaluation of tongue movement and/or tongue strength, for example, infant tongue movement and strength during nutritive suck (NS) and non-nutritive suck (NNS), are provided. The system and method may include an intervention directed at training the tongue movement and increasing NS tongue strength and/or NNS tongue strength of a subject with the intended outcome of positively impacting a transition from tube feedings to oral feedings by improving bottle feeding performance of the subject. The system, method and apparatus are configured to enable noninvasive direct measurement of the force of the tongue on the nipple interface and kinematic changes to the nipple during non-nutritive suck and nutritive suck and movement measurement. Broadly, the system, method and apparatus comprise providing deformable materials which may be associated with sensors, allowing measurement of the movement of the tongue and degree of deformation of the deformable materials, the amount of force induced, etc., such as during application of force by the tongue during sucking. Without intending any limitation, the deformable materials may be configured as or associated with a nipple shape of known configuration, such as an infant bottle nipple, a pacifier nipple, a breast nipple shield, and the like. The sensor or sensors may be calibrated such that signals provided by the sensors over time may be collected and analyzed to identify stages of the feeding process and to determine the magnitude and direction of forces applied by the tongue to the nipple and kinematic analysis of the applied forces may be performed to derive the power, impulse, and work performed by the tongue, and other measurements of tongue strength which may be derived from the sensor signals.

As used herein, "nutritive suck" refers to the process of a subject ("subject") feeding with a bottle or breast and receiving fluid. Therefore, a "nutritive suck" ("NS") condition is one where the nipple element and/or the apparatus including the instrumented nipple is configured such that liquid is passed through the nipple during a sucking event. For example, the NS nipple may define an aperture through which liquid in communication with the nipple aperture, which may be liquid in a bottle or other container to which the NS nipple is attached, may flow through the nipple into a subject's oral cavity during a sucking or feeding event. In nutritive suck the fluid is typically a substance ingested by the infant during feeding, such as infant formula, water, milk, etc. As used herein, fluid type is not meant to be limiting.

As used herein, "non-nutritive suck" refers to the process of a subject ("subject") performing the same task as nutritive feeding but not receiving fluid. A "non-nutritive suck" ("NNS") condition is one where liquid is not flowed through the nipple, e.g., no feeding occurs. The nipple in NNS may contain an aperture for passage of fluid or may be sealed. In a non-limiting example, a NNS nipple may be configured without an aperture such that fluid flow through the nipple is prevented. In another example, a NNS nipple may be configured as a pacifier. In another example, an evaluation apparatus may include a nipple with an aperture which may be used in either of a NS (liquid provided) condition or NNS (no liquid provided) condition.

As used herein, an "instrumented nipple" is a nipple element including, attached to or in selective communication with an insert, where the insert may include one or more of a compliance element, a sensor, and an intermediate device. As used herein, "compliance" is a nipple or nipple element's tendency to resist deformation caused by applied forces, for example, the forces applied by the subject's tongue against the nipple during sucking, and a "compliance element" is an insert configured to modify the compliance of an instrumented nipple including the compliance element relative to a nipple element which is not instrumented. As used herein, "tongue strength" refers to a singular measure or plurality of measures used to assess the ability of the tongue to perform its function. Tongue strength measures include but are not limited to force, impulse, power and work.

Referring to the drawings wherein like reference numbers represent like components throughout the several figures, the elements shown in FIGS. 1A-14 are not to scale or proportion. Accordingly, the particular dimensions and applications provided in the drawings presented herein are not to be considered limiting.

Figure 5A:
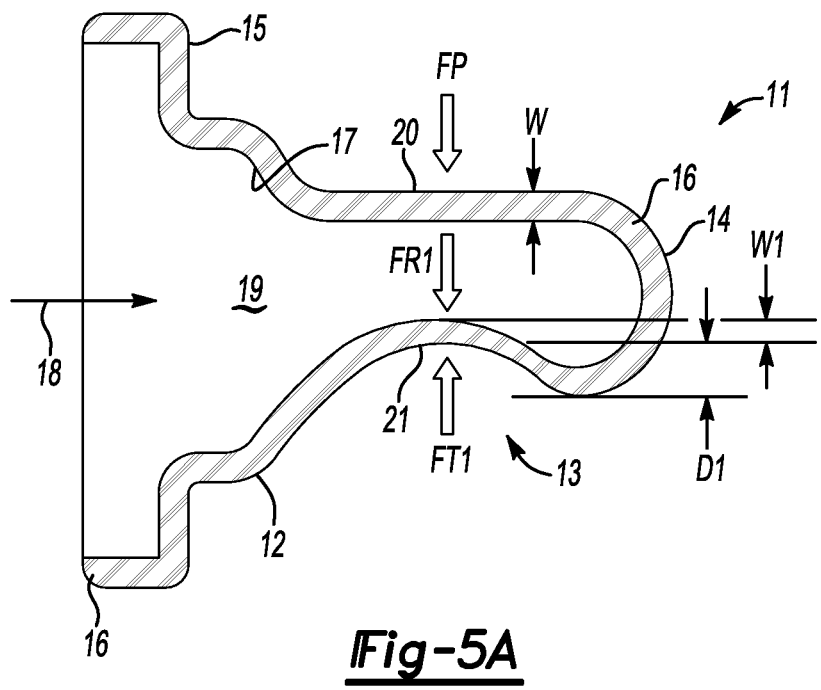
FIG. 5A is a schematic cross-sectional view of a nipple element and shown in a sucking condition.

Referring to FIG. 5A, shown is a schematic cross-sectional view of a nipple element generally indicated at 11. The nipple element 11 is shown in a sucking condition, e.g., in a deformed condition caused by a deformation force exerted on the nipple 11. The deformation force may be a tongue force FT exerted during sucking or feeding, or a calibration force FC exerted during a calibration process as described herein. The nipple element 11 is formed of a deformable material such as silicone, rubber, or other polymeric or natural material.

The nipple element 11 may be a standard nipple, e.g., a commercially available nipple configured as a pacifier or feeding nipple, also known as a bottle nipple. In another example, the nipple element 11 may be configured as a breast nipple shield which may be instrumented to provide an instrumented nipple 10 for use in evaluating tongue movement and/or strength in a NS configuration where the fluid source is a breast and the instrumented nipple 10 is placed in operative contact with the breast nipple. In a non-limiting example, the nipple element 11 may be configured for use with an infant.

The nipple element 11 may be configured as a non-infant (non-infant child or adult) pacifier and may be instrumented to provide an instrumented nipple 10 for use in evaluating the tongue movement, tongue strength and/or swallowing capabilities of a non-infant subject, for example, an elderly subject. In this example, the non-child nipple element 11 may be configured for either NS or NNS and adaptable to a fluid source or as otherwise described herein to enable evaluation of the subject's swallowing capability. It would be understood based on these examples that the configuration of the nipple 11 element shown in the figures is not intended to be limiting, and the nipple element 11 may be of a standard or commercially available configuration or a non-standard configuration. The nipple element 11 may be referred to herein as an unmodified nipple or as a non-instrumented nipple, in which case that the nipple element 11 refers to a standard nipple element, e.g., a nipple element, bottle nipple, breast nipple shield, etc. which has not been modified from its standard (commercially available) configuration or the nipple element 11 without instrumentation. A nipple element 11 may be combined with one or more inserts, as described in further detail herein, to provide an instrumented nipple 10.

In a typical configuration, the nipple element 11 includes a tip portion 14 at one end and a flange portion 15 at the opposing end. The tip portion 14 is adjacent the intermediate portion 13 of the nipple, also referred to herein as the nipple body 13. A base portion 12 is interposed between the body 13 and the flange portion 15. The nipple element 11 shown in FIGS. 1A and 5A is configured as a non-nutritive suck (NNS) nipple, such that the interior surface 17 of the nipple wall 16 defines a nipple cavity 19 which is enclosed at the tip 14 and in communication with an opening 18 defined by the flange portion 15. In a non-limiting example, the nipple element 11 may be configured as a pacifier and may include, as shown in FIG. 13C an extension 27 which may be provided as a handle for inserting, positioning and removing the nipple element 11 relative to a subject's oral cavity. The subject's oral cavity may also be referred to herein as the subject's mouth.

The nipple element 11 included in the instrumented nipple 10A shown in FIG. 1A is shown in a first condition, which may also be referred to herein as a resting or non-deformed condition. In the resting condition, minimal to no forces are exerted by the tongue on the nipple element 11 such that deformation of the nipple element 11 is minimal to none. A nipple element 11 is shown in FIG. 5A in a second condition, which may also be referred to herein as a sucking or deformed condition. In the sucking condition, the nipple is positioned in the subject's mouth such that a first portion 20 of the nipple element 11 is in contact with the subject's palate (not shown), and a constraining force FP is exerted by the palate against the first portion 20, which may be referred to herein as the palate facing portion of the nipple. During sucking, the subject's tongue (not shown) exerts a tongue force FT on a second portion 21 of the nipple element 11, shown in FIG. 1A as FTx and in FIG. 5A as FT1. The second portion 21 may be referred to herein as the tongue facing portion 21 of the nipple element 11 and generally opposes the palate facing portion 20 when the nipple is positioned in the subject's mouth. In a sucking condition, as shown in FIG. 5A, the tongue force FT compresses the nipple element 11 by deforming wall 16 of the tongue facing portion 21 toward the palate facing portion 20. The magnitude of the deformation, which may be measured by a deformation distance D, is shown as D1 for the sucking condition shown in FIG. 5A. It would be understood that the deformation distance D of the nipple in the resting condition shown in FIG. 1A is zero.

The nipple element 11 exerts a resistive force FR in opposition to the tongue force FT. The resistive force FR is a function of the compliance of the nipple element 11, e.g., the nipple's tendency to resist deformation caused by applied forces such as the tongue force FT. The compliance of the nipple element 11 and the resistive force FR may be determined by one of more factors, including but not limited to the material characteristics of the nipple element 11, including the material type, elasticity, hardness, etc., and the wall thickness W of the wall 16. As shown in FIGS. 5B through 12B, the effective compliance of the nipple element 11 and the resistive force FR may be modified by changing the configuration of the wall 16 in the tongue facing portion 21 and/or adding a compliance element configured to exert a resistive force FR in opposition to a tongue force FT to provide an instrumented nipple 10B. As described in further detail herein, instrumented nipples 10 of varying compliance and resistive force FR may be used in an intervention method as shown in FIG. 14 to develop tongue strength in a user subject such as an infant, which may be a preterm infant.

Deformation forces exerted on a nipple in a sucking condition can be evaluated by instrumentation of the nipple element 11 using an insert including or configured as a sensing device, such as but not limited to a sensing device 30 described in further detail herein and illustrated by the figures, to provide an instrumented nipple 10. The compliance and/or resistive force of a nipple may be modified by instrumentation of the nipple element 11 using an insert including or configured as a compliance element having a known compliance and resistive force FR, such as but not limited to a compliance element 80 described in further detail herein and illustrated by the figures, to provide an instrumented nipple 10. The known compliance and/or resistive force FR may be determined by configuration of the instrumented nipple 10, or by calibration of the instrumented nipple 10 using a calibration apparatus 60 as provided herein. The term "instrumented nipple," as used herein, refers to a nipple including or in operative communication with at least one insert, where the insert may be a sensing device 30, a compliance element 80, an intermediate device 37, a combination of two or more of these, or a nipple which is otherwise configured to include an insert configured to directly measure the deformation force exerted on the nipple and/or to provide a nipple characterized by a known compliance or calibrated resistive force FR.

Figure 2B:
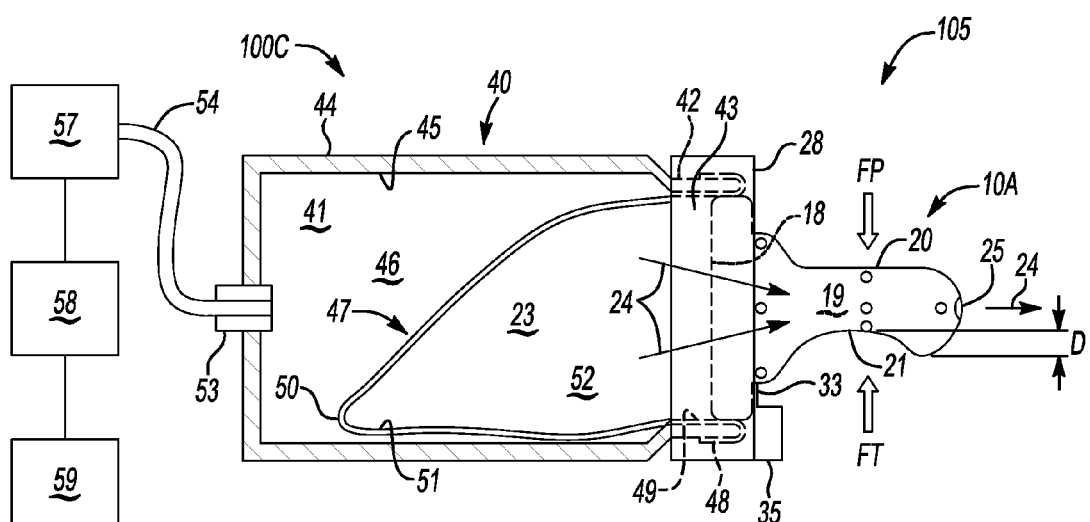
FIG. 2B is a schematic illustration of the tongue movement evaluation system including a second example of a tongue movement evaluation apparatus.

In a first non-limiting example, FIGS. 1A through 1D show an instrumented nipple 10A including a nipple element 11 and an insert configured as a sensing device 30A. The sensing device 30A includes a sensor array 31 consisting of a plurality of sensors 32. In the non-limiting example shown, each sensor 32 includes a piezoelectric crystal. Each of the piezoelectric sensors 32 is positioned in communication with the wall 16 of the nipple element 11. Each piezoelectric sensor 32 may be positioned, for example, by adhering, bonding, embedding, submerging, bracing, fixturing using a mechanical fixture or support device or otherwise affixing or positioning the piezoelectric sensor 32 to the inner wall surface 17 or within the wall 16 in a specified location. For example and as shown in FIGS. 1A-1D, the plurality of sensors 32 may include groups of sensors 32a, 32b, 32c. The first group of sensors 32 may include one or more piezoelectric sensors 32a1 ... 32an arranged in the base portion 12 of the nipple element 11, where little to no movement of the nipple element 11 occurs during sucking. The second group of one or more piezoelectric sensors 32b may include one or more piezoelectric sensors 32b1 ... 32bn arranged in the body portion 13 of the nipple element 11, where substantial movement of the nipple element 11 occurs during sucking, as shown in FIG. 2B, which shows the instrumented nipple 10A in a sucking condition. The third group of one or more piezoelectric sensors 32c1 ... 32cn may be arranged in the tip portion 14 of the nipple element 11. The first, second and third groups of piezoelectric sensors 32A, 32B, 32C form the sensor array 31 shown in FIGS. 1C and 1D in a resting condition. Each of the piezoelectric sensors 32n is identifiable to a set of coordinates X, Y, Z describing the position of the respective piezoelectric sensor 32 in the array 31. For example and referring to FIGS. 1C and 1D, the sensor 32a3 is identifiable to coordinates X1, Y1, Z1 in the array 31. Likewise, sensor 32b4 is identifiable to coordinates X2, Y2, Z2, sensor 32b2 is identifiable to coordinates X3, Y3, Z3, and so on. (Note, Z2 and Z3 are not shown in FIG. 1C for clarity) It is understood that the values of X, Y, and Z will change as the position of the corresponding crystal sensor 32n changes during deformation of the instrumented nipple 10A. The number, grouping, location, arrangement, means of attachment and/or positioning of piezoelectric sensors 32 in the array 31 is intended to be non-limiting, and other arrangements of a plurality of sensors 32 and/or configurations of the array 31 may be used in collecting sucking deformation data from an instrumented nipple 10A.

Each of the piezoelectric sensors 32 may be operatively connected to a lead 33, which may be, for example, a conductive wire configured to conduct electrical signals from each sensor 32 to a data collector/analyzer 59 (see FIG. 2A) which may, in the present example, be configured as sonomicrometry instrumentation for use in performing kinematic analysis of the signals received from each sensor 32 over time during a feeding or sucking event. The leads 33 may be connected directly to the data collector/analyzer 59, or may be operatively connected to a communications interface 35 configured to transmit the signals from sensors 32 to the data collector/analyzer 59. The communications interface 35 may be, by way of non-limiting example, a connector receiving the plurality of leads 33 and connectable to the data collector/analyzer 59 or a portable data storage device (not shown) such as a SIM card, flash drive, etc. which may include RAM or flash memory and be used to transfer the collected data to the data collector/analyzer 59. The plurality of leads 33 may be routed through a conduit 34, for ease of handling and/or to protect the leads from damage, etc., as shown in FIGS. 1B and 2B. In another example shown in FIG. 2B, the sensors 32 or communications interface 35 may be configured for wireless transmission of the sensor signals 32 to the data collector/analyzer 59 using any suitable means of wireless transmission such as Bluetooth®, RFID, Wi-Fi, ZigBee® or other wireless methods. Further, the data signals can be processed, displayed, transferred to a processor for additional analysis, stored in memory, etc.

A substance 24 is provided to the nipple cavity 19 such that the plurality of piezoelectric crystal sensors 32 are submerged or otherwise inter-operatively connected through the substance 24 to allow sound waves to travel between the submerged piezoelectric crystal sensors 32. The substance 24 may be, by way of non-limiting example, a saline solution, liquid, gas, deformable solid or a combination of these which is capable of transmitting sound waves between the piezoelectric crystal sensors 32 collectively contained by the substance 24. In one example, the piezoelectric crystal sensors 32 may be embedded in the wall 16 such that the substance 24 is the material from which the nipple is made, e.g., the wall material, and sound waves are transmitted between the embedded crystal sensors 32 through the material of the nipple wall 16. The instrumented nipple 10A may be configured as a NNS nipple, as shown in FIGS. 1A and 2A, or as a NS nipple as shown in FIGS. 1C and 2B. In the latter example, the instrumented nipple 10A configured as a NS nipple may include an aperture 25 at the tip end of the nipple element 11, such that the substance 24 may flow through the nipple element 11, into the subject's oral cavity during a feeding or sucking event. In this example, the substance 24 may be a nutritive substance such as a water, formula or milk based substance, provided to the nipple cavity 19 in sufficient volume during a feeding or sucking event to continuously submerge the plurality of sensors 32 during an evaluation sequence, as shown in and described for FIG. 2B.

Referring again to FIG. 1A, the instrumented nipple 10A may be configured as a NNS nipple, wherein the instrumented nipple 10A includes a non-permeable membrane 22 operatively and sealably connected to nipple element 11 to enclose the opening 18, thereby containing the substance 24 in the nipple cavity 19 and forming a first sealed chamber 23. The non-permeable membrane 22 may be flexible, such that pressure changes within the first sealed chamber 23 may be transmitted through the membrane 22. As shown in FIG. 2A, the plurality of leads 33 may be extended from the plurality of sensors 32 in the sealed chamber 23 through the nipple wall 16 or membrane 22 in a sealed manner to the data analyzer/collector 59, which may be via the communications interface 35. In a non-limiting example, the instrumented nipple 10A configured as shown in FIGS. 1A and 1B may be used as a pacifier-type evaluation apparatus 100A to collect data during an evaluation sequence, during which the instrumented nipple 10A is provided to a subject for collection of data during sucking. In other non-limiting examples, the NNS instrumented nipple 10A shown in FIG. 1A may be included in the NNS evaluation apparatus 100B shown in FIG. 2A, and the NS instrumented nipple 10A shown in FIG. 1C may be included in the NS evaluation apparatus 100C shown in FIG. 2B. The data may be collected over a period of time and may include data representing a plurality of sucking cycles.

Deformation of the instrumented nipple 10A by the subject's tongue during the evaluation sequence will cause deformation of the sealed chamber 23 resulting in a change in kinematics of the plurality of piezoelectric sensors 32 and deformation of the sensor array 31, as illustrated in FIG. 2B. Sound waves transmitted and received between the sensors 32 in the array 31 during the deformation and evaluation sequence are output in real time as electrical signals and measured using the sonomicrometry instrumentation included in the data collector/analyzer 59. Knowing the speed at which sound waves travel within the connecting substance 24 between the respective crystal sensors 32 of the array 31 allows calculation of the instantaneous distances between all the crystal sensors 32 in real time using the established technology of sonomicrometry. Using triangulation or trilateralization, the three-dimensional kinematics of the crystal sensors 32 can be determined, including the positional coordinates X, Y, Z of each crystal sensor $32n$ in the array 31 at each measured point in time.

Alteration to the kinematics of the crystal sensors 32 is a direct result of forces FT applied by the tongue against the instrumented nipple 10A as the instrumented nipple 10A is constrained against the palate of the subject's mouth by a palate force FP. By placing the crystal sensors 32 in a known array 31, signal data collected from the crystal sensors 32 may be used to determine the direction at which force is applied to the instrumented nipple 10A using basic physics principles. Inverse dynamics can further interpret force vector components FTx, FTy, FTz (not shown for clarity) of the tongue force FT and be clinically interpreted to the muscles of the tongue.

When the properties of the nipple materials and sound conducting substance 24 are known, for example, through testing properties such as mass, compliance and viscosity, the forces exerted on the nipple 10A during deformation can be derived using the acceleration of the crystal sensors 32 independent of a sensor signal calibrated to the deformation of the instrumented nipple 10A.

Figure 3A:
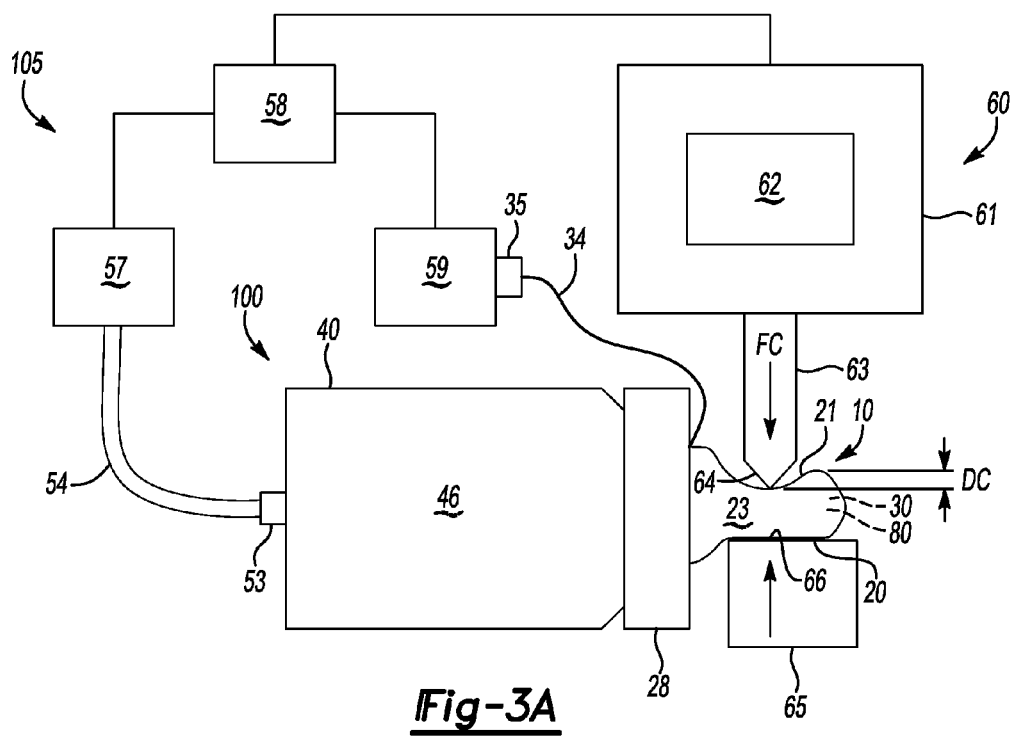
FIG. 3A is a schematic illustration of a calibration apparatus for calibrating the tongue movement evaluation apparatus or an instrumented nipple.

Referring to FIGS. 2A-4C, an instrumented tongue strength evaluation apparatus 100 ("evaluation apparatus") may be calibrated using a calibration apparatus, such as the calibration apparatus 60 shown in FIG. 3A to calculate the magnitude of force applied to the instrumented nipple 10 in relation to the deformation of the nipple 10. Forces applied by the tongue during evaluation of a subject correspond to the following equation:

$$FT \propto DT \cong FC \propto DC \propto \text{Nipple Compliance} \qquad (1)$$

where FT are the forces produced by the tongue on an instrumented nipple 10, DT are the distances the nipple deforms due to the tongue, such as D1 shown in FIG. 5A, FC are the forces applied to the instrumented nipple 10 during a calibration procedure to deform the instrumented nipple 10, where the distances the nipple deforms due to the calibration force are DC, as shown in FIG. 3A. Measurement of changes in pressure within the sealed chamber 23, obtained, for example, from the evaluation system 105 and evaluation apparatus 100A shown in FIG. 2A using the calibration apparatus 60 shown in FIG. 3A, may be used in conjunction with or independent of the kinematics of the crystal sensor array 31 to calibrate the instrumented nipple 10A. It would be understood that calibration does not need to be performed for every nipple or at every instance of use, for example, when the properties of the nipple are known or established.

Referring now to FIG. 2A, shown is a tongue movement evaluation system generally indicated at 105. The evaluation system 105 includes a sensor data collector/analyzer 59 and a pressure gauge 57 in communication with a processor 58 and a tongue movement evaluation apparatus 100B, using wired or wireless communication methods. The collector/analyzer 59 in the present example may be configured as a sonomicrometer or include sonomicrometry instrumentation for analyzing data collected from the plurality of piezoelectric crystal sensors 32 included in the instrumented nipple 10A of the apparatus 100B. Each of the gauge 57, processor 58 and collector/analyzer 59 may include or be in operative communication with memory, which may be configured as one or more of Read Only Memory (ROM), Random Access Memory (RAM), electrically-erasable programmable read only memory (EEPROM), etc., of a size and speed sufficient for executing the functions performed by the respective gauge 57, processor 58 and collector/analyzer 59. Each of the gauge 57, processor 58 and collector/analyzer 59 may include a user interface, which may include a display and/or input/output interface for communicating data, analysis results, messages, etc. The configuration shown in FIG. 2A is not intended to be limiting, and it would be understood that functions performed by each of the elements 57, 58, 59 may be performed by another of the elements 57, 58, 59 as configured to do so. For example, the sensor data collector/analyzer 59 may be configured to also perform functions of the processor 58.

The evaluation apparatus 100B, in a non-limiting example, is configured for non-nutritive suck (NNS) and includes the instrumented nipple 10A including the sensing device 30A and configured as shown in FIG. 1A, where a sensor array 31 is submerged in the conducting substance 24 contained in a first sealed chamber 23 formed by the nipple cavity 19 and enclosed by the membrane 22 (see FIG. 1A). The instrumented nipple 10A is sealably connected to a container 40, which in the non-limiting example shown may be configured as an infant feeding bottle, commonly referred to as a baby bottle. The bottle 40 includes a bottle cavity 41 defined by the inner surface 45 of the bottle wall 44. Sealing contact may be provided by retaining the flange portion 15 of the instrumented nipple 10A against the bottle opening 43 using a collar 28 selectively connected to the end portion 42 of the bottle 40. The collar 28 may be, in the example shown, a standard bottle collar used with an infant feeding bottle or a ring-shaped retainer threadable onto the end portion 42 to retain the instrumented nipple 10A in sealing contact with the bottle 40. As shown in FIG. 2A, a second sealed chamber 46 is defined by the bottle cavity 41 enclosed by the instrumented nipple 10A, such that the first sealed chamber 23 and the second sealed chamber 46 are separated by the membrane 22, e.g., the membrane 22 is in operative communication with both the first and second sealed chambers 23, 46. The membrane 22 may be configured as a flexible non-permeable membrane such that changes in pressure in the first sealed chamber 23, such as pressure changes occurring during nipple deformation, may be transmitted through the membrane 22 to proportionally change the pressure in the second sealed chamber 46.

An intermediary tube 54 may be in fluid communication with the second sealed chamber 46 at a first tube end 55, and in fluid communication with the pressure gauge 57 at a second tube end 56, such that changes in pressure in the second sealed chamber 46 may be measured and collected by the pressure gauge 57. The pressure gauge 57 may include an analog/digital (A/D) transducer (not shown) for conversion of the pressure signal to an electronic signal, such that pressure measurements may be transmitted to and/or collected by the processor 58, stored as data, etc. The bottle 40 may include an adapter 53 configured to receive the first tube end 55 and position the intermediary tube 54 in fluid communication with the second sealed cavity 46.

Deformation of the instrumented nipple 10A will result in a deformation of the first sealed chamber 23 resulting in a change in pressure in the first sealed chamber 23 and movement of the flexible membrane 22, which results in a corresponding change in pressure in the second sealed chamber 46. The corresponding change in pressure in the second sealed chamber 46 may be recorded. The pressure data may be collected by the pressure gauge 57 and used in conjunction with the kinematics data collected from the sensor array 31 and provided by the sonomicrometry instrumentation of the sensor data collector/analyzer 59 to evaluate the deformation force (magnitude and direction) being applied to a calibrated instrumented nipple 10A. The NNS evaluation apparatus 100B and instrumented nipple 10A may be calibrated as shown in and described for FIGS. 3A and 3B.

Referring now to FIG. 2B, shown is the tongue movement evaluation system 105 as described for FIG. 2A, shown in use with a tongue movement evaluation apparatus 100C. The evaluation apparatus 100C, in a non-limiting example, is configured for nutritive suck (NS) and includes the instrumented nipple 10A including the sensing device 30A and shown in a sucking condition in FIG. 2B. The NS instrumented nipple 10A is configured as shown in FIG. 1A, where the nipple tip portion 14 defines an aperture 25 configured to allow flow through of the substance 24 from the nipple cavity 19. In the present example, the substance 24 may be a liquid nutritive substance, such as a water or infant formula based substance, which is provided in adequate supply from a flexible container 47 housed in the bottle cavity 41 to submerge the sensor array 31 sufficiently during deformation of the instrumented nipple 10A to allow conduction of sound waves between the piezoelectric crystal sensors 32 of the sensor array 31.

As shown in FIG. 2B, the evaluation apparatus 100C includes a flexible container 47 including an end portion 48 which defines a container opening 49. The wall 50 of the flexible container 47 is non-permeable, and the interior surface 51 of the wall 50 defines a container cavity 52. The end portion 48 of the flexible container 47 is positioned as generally shown in FIG. 2B to overlap the end portion 42 of the bottle 40, such that when the instrumented nipple 10A is sealably attached to the bottle 40 using the collar 28, the container cavity 52 is in fluid communication with the nipple cavity 19. The container cavity 52 may be at least partially filled with the substance 24 before sealing the container cavity 52 in communication with the nipple cavity 19, such that the evaluation apparatus can be positioned during deformation of the instrumented nipple 10A, e.g., during a calibration or nutritive sucking event, to flow the substance 24 from the container cavity 52 to the nipple cavity 19 and through the aperture 25, thereby submerging the sensor array 31 in the substance 24 to allow conduction of sound waves through the substance 24 during nutritive sucking. The first sealed chamber 23 is formed by the cavities 19, 52 in fluid communication with each other. Deformation of the instrumented nipple 10A during nutritive sucking or calibration causes a change in pressure in the first sealed chamber 23.

As shown in FIG. 2B, a second sealed chamber 46 is defined by the bottle wall surface 45 and the portion of the wall 50 of the flexible container housed in the bottle cavity 41, such that the first sealed chamber 23 and the second sealed chamber 46 are separated by the flexible container wall 50, e.g., the flexible wall 50 is in operative communication with both the first and second sealed chambers 23, 46. The flexible container 47 may be configured such that changes in pressure in the first sealed chamber 23, such as pressure changes occurring due to nipple deformation during nutritive sucking or calibration, may be transmitted through the flexible container wall 50 to proportionally change the pressure in the second sealed chamber 46.

As described for FIG. 2A, deformation of the instrumented nipple 10A will result in a deformation of the first sealed chamber 23 resulting in a change in pressure in the first sealed chamber 23 and movement of the flexible container wall 50, which results in a corresponding change in pressure in the second sealed chamber 46. The corresponding change in pressure in the second sealed chamber 46 is recorded by the pressure gauge 57. The pressure data collected by the pressure gauge 57 may be used in conjunction with or independent of the kinematics data collected from the sensor array 31 and provided by the sonomicrometry instrumentation of the sensor data collector/analyzer 59 to evaluate the deformation force (magnitude and direction) being applied to an instrumented nipple 10A. The NS evaluation apparatus 100C and instrumented nipple 10A may be calibrated as shown in and described for FIGS. 3A and 3B.

Referring now to FIG. 3A, shown is a calibration apparatus 60 which may be used to calibrate an instrumented nipple 10 and/or an evaluation apparatus 100 to calculate the magnitude of deformation force applied to the nipple in relation to the pressure change in the nipple cavity, the depth of deformation D, the sensor output of a sensing device 30 which may be included in the instrumented nipple 10, and/or the resistive force FR exerted by a compliance element 80 which may be included in the instrumented nipple 10. As shown in FIG. 3A, the calibration apparatus 60 may include an indenter 63 operatively connected to the force delivering device 61 and configured to deliver a known calibration force FC to the instrumented nipple 10. The force delivering device 61 may be configured using any suitable means to deliver a calibration force FC to the instrumented nipple 10. In one example, the force delivering device 61 may be configured as or include a hand held or mechanically driven force gauge, a force transducer, a strain gauge, a pressure gauge, an accelerometer, or a combination of these. The indenter 63 includes a contact interface 64 for making contact with the instrumented nipple 10, which may be oriented such that contact interface 64 contacts the tongue facing portion 21 of the instrumented nipple 10 when applying a force to the nipple 10, where the instrumented nipple 10 may be positioned on a platen 65 with the palate facing portion 20 of the nipple 10 in contact with the platen surface 66. The contact interface 64 may be configured to provide a predetermined pattern or area of contact with the tongue facing portion 21 of the nipple 10 during force application. In a non-limiting example, the contact interface 64 may be semi-spherical to simulate an infant tongue in contact with the nipple during force application. The instrumented nipple 10 is positioned on the platen 65 such that the palate facing portion 20 of the nipple 10 is in contact with the platen surface 66 during force application, and the platen surface 66 provides an opposing force corresponding to the palate force FP (see FIG. 1A) exerted by the subject's palate when the nipple 10 is positioned in the subject's mouth in a feeding session. The platen surface 66 may be substantially flat, or in a non-limiting example may be contoured to simulate the palate interface.

Figure 3B:
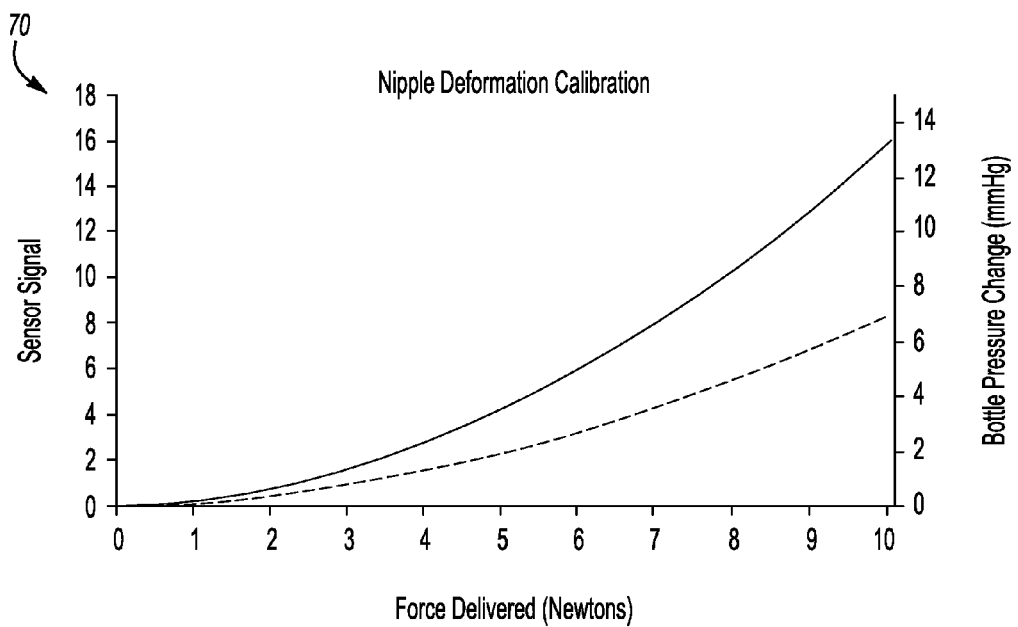
FIG. 3B is a schematic illustration of calibration data collected from the tongue movement evaluation apparatus of FIG. 3A using the calibration apparatus of FIG. 3A.

The force delivering device 61 may include a user interface 62 which may be configured to display the calibration information, including the force F exerted on the instrumented nipple 10 by the indenter 63, the depth of deformation D, the pressure change in the second sealed chamber 46 measured by the pressure gauge 57, the sensor data collected from a sensing device 30 included in the instrumented nipple 10 by the sensor data collector/analyzer 59 during a calibration event, the calibration results provided by the processor 58, etc. In one example, an evaluation apparatus 100 including an instrumented nipple 10 may be positioned relative to the calibration apparatus 60 as shown in FIG. 3B. The evaluation apparatus 100 may be configured as a NNS or as a NS apparatus, as described for FIGS. 2A and 2B, respectively. The instrumented nipple 10 may include at least one of a compliance element 80, as described in further detail herein, and/or at least one sensing device 30. By way of non-limiting example, the sensing device may be a piezoelectric crystal sensing device 30A, as described for FIGS. 1A-2B, or may be another sensing device 30, as described in further detail herein. In a NNS configuration or other configuration where fluid is not required, for example, as a conducting substance, the evaluation apparatus may be configured without a membrane 22 or flexible container 47 such that the bottle cavity 41 and the nipple cavity 19 may be in fluid communication with each other, and the bottle cavity 41 and nipple cavity 19 together define a sealed chamber, such that the pressure change in the sealed chamber defined by the bottle cavity 41 and nipple cavity 19 may be measured by the pressure gauge 57 in fluid communication with the sealed chamber thus defined.

A known calibration force FC may be applied to the instrumented nipple 10 using the force delivering device 61. Application of the known calibration force FC results in deformation of the instrumented nipple 10 and nipple cavity 19, which produces a change in the pressure of the first and second sealed chambers 23, 46 which is measured using the pressure gauge 57 during force application. Deformation of the nipple 10 by the calibration force FC produces a change in the output of the sensing device 30 in communication with the nipple 10, and the output of the sensing device 30 is measured and collected using the sensor data collector/analyzer 59.

The calibration graph 70 shown in FIG. 3B illustrates an example of sensor signal data (shown as the solid line) and pressure change data (shown by the dashed line) collected during the calibration process corresponding to varying magnitude of applied calibration force FC. Other sensor measurements, such as the deformation distance D, may be collected and analyzed in the calibration process. In a first example, the instrumented nipple 10 and/or the evaluation apparatus 100 may be calibrated using the pressure change data collected by the pressure gage 57 and the applied deformation force data collected from the force delivering device 61 during the calibration sequence to perform the calibration. In another example, the instrumented nipple 10 and/or the evaluation apparatus 100 may be calibrated using the movement measurement output data collected from the sensing device 30 and the applied deformation force data collected from the force delivering device 61 during the calibration sequence to perform the calibration. In another example, the calibration may be performed using the pressure change data, the applied deformation force data and the movement measurement output data to perform the calibration.

The calibrated evaluation apparatus 100 may be used during an evaluation sequence, which may be a NS or NNS sucking sequence, to collect data for evaluation of a subject's tongue movement and/or strength. During an evaluation sequence and over time or at time intervals, movement measurement data may be collected from the sensing device 30 and/or pressure data may be collected from the pressure gage 57, or both may be collected concurrently or independently. The Table 71 of FIG. 4A is an illustrative example of kinematic data collected at defined time intervals during a subject's evaluation sequence from a sensing device 30A including a piezoelectric crystal sensor array such as the sensor array 31 shown in FIGS. 1A-1D. During the evaluation sequence, pressure data may be collected concurrently with collection of sensor data from the sensing device 30A.

Graph 72 of FIG. 4B shows an illustrative example of normalized pressure data collected during a sucking evaluation sequence from a first subject and a second subject using a NNS evaluation apparatus, for example, the apparatus 100B shown in FIG. 2A, and includes a plurality of sucking cycles, which may also be referred to herein as deformation cycles. In the example shown in graph 72, the pressure data illustrated by the solid line represents data collected from the NNS evaluation apparatus 100B used with a first subject, where tongue movement of the first subject may satisfy a tongue movement objective or NNS force or strength threshold (not shown). The pressure data illustrated by the broken line in graph 72 represents data collected from the NNS evaluation apparatus 100B used with a second subject, where the tongue movement of the second subject may not meet the tongue movement objective or NNS force or strength threshold. The data shown is illustrative and non-limiting.

Graph 73 of FIG. 4C shows an illustrative example of normalized and non-normalized pressure data collected during a sucking evaluation sequence from a subject using a NS evaluation apparatus, for example, the apparatus 100C shown in FIG. 2B, and includes a plurality of sucking cycles, which may also be referred to herein as deformation cycles. In the example shown in graph 73, the pressure data illustrated by the solid line represents data collected from the NS evaluation apparatus 100C used with a first subject, where tongue movement of the first subject may satisfy a tongue movement objective or NS force or strength threshold (not shown). The pressure data illustrated by the broken line in graph 73 represents data collected from the NS evaluation apparatus 100C used with a second subject, where the tongue movement of the second subject may not meet the tongue movement objective or NS force or strength threshold. The data shown is illustrative and non-limiting.

The collected data may be analyzed for evaluation and measurement of the tongue movement and/or force exerted by the subject on the instrumented nipple 10 during the stages of sucking, from which measurements of tongue strength such as work performed, impulse, power, sucking frequency, rate of force production, rate of tongue movement, deformation distance, or other strength measures may be derived. Further analysis may include evaluation of sucking frequency and/or rate, rate of exerted force (exerted force measured over time), deformation rate (deformation distance over time) or other parameters measured over the time period of the sucking session which may be used, for example, to quantify fatigue.

The evaluation system 105 and evaluation apparatus 100 can be used with a subject in a noninvasive manner to accurately collect, model and quantify the tongue movement, tongue force, and/or sucking behavior of a subject, which may include determining the deformation forces exerted by the subject on the instrumented nipple 10 during an evaluation sequence, which may include a sucking sequence. Both NS and NNS sequences may be evaluated for a subject. In an intervention method 110 illustrated in FIG. 14 and described in further detail herein, one or more instrumented nipples 10 having a known compliance may be used to evaluate and develop a subject's tongue strength.

Various configurations of instrumented nipples 10, each having a known compliance, and which may include, by way of non-limiting example, instrumented nipples 10A . . . 10H illustrated by FIGS. 1A-1D and 5B-12B, may be used in the noninvasive methods described herein to provide a direct measurement of tongue movement and/or force and evaluation of tongue movement and/or strength. Various types of sensors and configurations of sensing devices 30 and/or compliance elements 80 may be used for instrumenting an instrumented nipple 10. Sensing devices 30 and sensor types may include but not be limited to contact and non-contact strain gages, piezoelectric crystals, piezoelectric films or other piezoelectric material, piezoresistive material, accelerometers, force transducers, microstrain displacement/position sensors, differential variable reluctance transducers (DVTR) and the like. A sensor may be adhered, bonded, glued, inserted within the nipple cavity 19, sutured or tied to a portion of the nipple, affixed, clamped, fixtured or otherwise attached to or positioned in operative contact or communication with a portion of the nipple such that deformation forces exerted on the nipple may be measured or otherwise evaluated. The sensor or sensing device 30 including the sensor may be configured to provide an output signal, which may be measurable or observable as a sound wave, an electrical signal, an optical signal, a pressure, a strain, a visual indicator or combination of these. An instrumented nipple 10 may include more than one sensor or sensing device 30, where the plurality of sensors or sensing devices 30 may be arranged in the nipple cavity 19 to measure the deformation force exerted in more than one location in the nipple cavity 19. The examples of sensor and sensing device types and configurations provided herein are intended to be illustrative and non-limiting.

Various types of compliance elements 80 may be used to provide an instrumented nipple 10. A compliance element 80 may be integral or non-integral to the nipple structure, and may be adhered, bonded, glued, inserted within the nipple cavity 19, sutured or tied to a portion of the nipple, affixed, clamped, fixtured or otherwise attached to or positioned in operative contact or communication with a portion of the nipple element 11 such that the compliance element 80 modifies the compliance of the nipple element 11 to provide an instrumented nipple 10 having a compliance which is known or determinable by calibration. The compliance element 80 may include or be formed of a deformable material such that the compliance element 80 is deformed as the instrumented nipple 10 is deformed. The deformable material may be a polymer-based material. In one example, the deformable material may be silicone. The deformable material may have defined or known characteristics such that the deformable material is configured to systematically move, strain, or otherwise deform relative to the forces applied to the instrumented nipple 10, and/or to provide a known resistive force FR. The compliance element 80 may be configured to provide a resistive force FR which may be linear or non-linear. The compliance element 80 may be configured to plastically deform above a predetermined level of applied tongue force FT, to provide a visual indicator. The predetermined level at which the visual indicator is provided may correspond to a tongue movement threshold or tongue strength objective established for the subject related to the evaluation method 110 shown in FIG. 14. The tongue movement threshold or tongue strength objective may correspond to the minimum tongue force required for successful NNS or NS sucking or nutritive feeding, successful swallowing, or the like. The examples of compliance element types and configurations provided herein are intended to be illustrative and non-limiting.

Figure 5B:
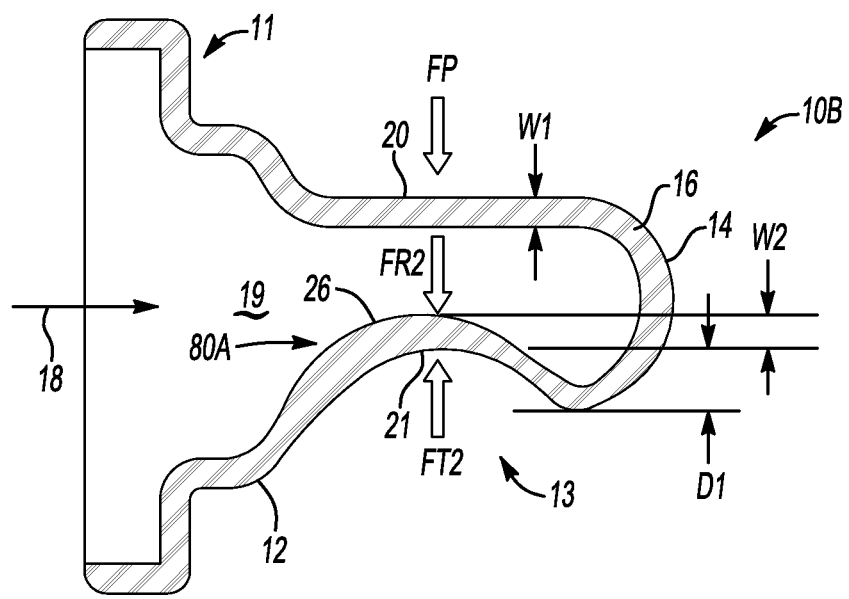
FIG. 5B is a schematic cross-sectional view of an instrumented nipple including an integral compliance element and shown in a sucking condition.

Referring now to FIGS. 5A and 5B, a non-instrumented nipple element 11 is shown in FIG. 5A and an instrumented nipple 10B is shown in FIG. 5B, where each is shown in a sucking condition. The nipple element 11 of FIG. 5A includes a tongue facing portion 21 having a wall thickness W1. As shown in FIG. 5A, in the sucking condition, a tongue force FT1 compresses the non-instrumented nipple element 11 and deforms the tongue facing portion 21 toward the palate facing portion 20. The magnitude of the deformation resulting from the applied tongue force FT1, which may be measured by a deformation distance D, is D1 in the present example. A resistive force FR1 is exerted by the non-instrumented nipple element 11 in opposition to the tongue force FT1, where the resistive force FR1 is a function of the compliance of the non-instrumented nipple element 11, e.g., the nipple's tendency to resist deformation caused by applied forces such as the tongue force FT1.

The instrumented nipple 10B includes a compliance element 80A which is configured to decrease the compliance of the tongue facing portion 21 of the instrumented nipple 10B such that the instrumented nipple 10B exerts a resistive force FR2 in opposition to an applied tongue force FT2. The integral compliance element 80A is formed by thickening the wall 16 of the tongue facing portion 21 to an effective or total wall thickness W2, such that W2>W1. The compliance element 80A may be formed by molding the instrumented nipple 10 to provide additional material 26 in the tongue facing portion 21 to form the compliance element 80A. By way of example, the compliance element 80A may be provided by adhering, bonding, or otherwise attaching the additional material 26 to the nipple wall surface 17 of the tongue facing portion 21. The material 26 may be the same material as the nipple element 11, or may be a different material as required to achieve the desired level of compliance of the instrumented nipple 10B. The integral compliance element 80A deforms when the nipple 10B is deformed. The effective wall thickness W2 increases the resistive force FR2 of the nipple 10B such that FR2>FR1, and the compliance of the instrumented nipple 10B is less than the compliance of the non-instrumented nipple element 11 shown in FIG. 5A.

The calibration apparatus 60 may be used to determine the compliance level of the instrumented nipple 10B relative to the non-instrumented nipple element 11. For example, the force delivering device 61 may be used to measure a calibration force FC1 required to deform the non-instrumented nipple element 11 to the deformation distance D1, where FC1∝FR1. The force delivering device 61 may then be used to measure a calibration force FC2 required to deform the non-instrumented nipple element 11 to the same deformation distance D1, where FC2∝FR2, and the ratio of FC2/FC1 is proportional to FR2/FR1 to provide a relative indication of the compliance increase of the instrumented nipple 10B relative to the non-instrumented nipple element 11. Because the compliance of the instrumented nipple 10B is less than that of the non-instrumented nipple element 11, the tongue force FT required to deform the nipple 10B in a sucking condition is increased from FT1 to FT2. The instrumented nipple 10B may be used, for example, in the intervention method 110 shown in FIG. 14, to exercise and strengthen the subject's tongue, e.g., to train the subject to achieve the same level of deformation D1 by increasing the subject's tongue strength from FT1 to FT2.

Figure 6A:
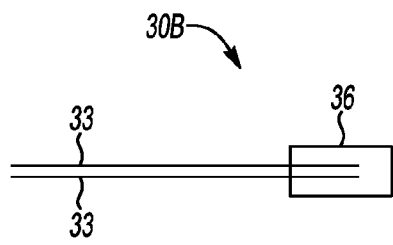
FIG. 6A is a schematic top view of a second example of an insert configured as a sensing device.
Figure 6B:
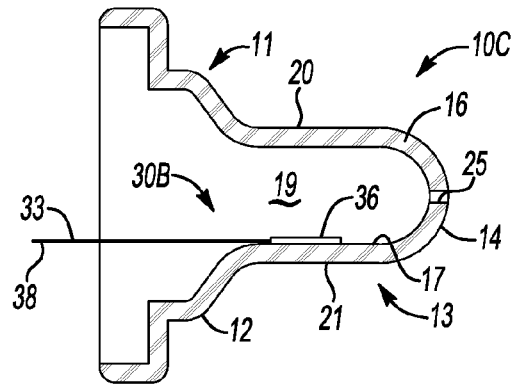
FIG. 6B is a schematic cross-sectional illustration of an instrumented nipple including the sensing device of FIG. 6A.

Referring now to FIGS. 6A and 6B, shown is another example of an instrumented nipple 10C which includes a sensing device 30B. The sensing device 30B includes a sensor 36, which in the non-limiting example shown may be configured as a strain gage. In use, the sensor 36 is operatively attached to the wall surface 17 of the tongue facing portion 21 of the nipple element 11, or positioned relative to (in contact with or immediately adjacent to) the wall of the nipple element 11, such that deformation forces exerted on the nipple wall 16 may be detected by the sensor 36, thereby providing an instrumented nipple 10C. Leads 33 are provided in operative communication with the sensor 36 and may be configured such that ends 38 may be operatively connected to a communication interface 35 or to a sensor data collector/analyzer 59, to provide direct measurement of an output signal provided by the sensor 36 in response to an applied deformation force. In the present example, the sensor 36 is configured as a strain gage operatively attached to the wall surface 17 adjacent the tongue facing portion 21 of the instrumented nipple 10C. It would be understood that other forms of sensors, included but not limited to piezoelectric crystals, piezoelectric films or other piezoelectric material, piezoresistive material, accelerometers, and force transducers, may be used. As a tongue force TF is applied to the tongue facing portion 21, the nipple 10 distorts from a resting condition into a sucking condition and the strain gage 36 is deformed to provide an output signal proportional to the applied tongue force TF. The instrumented nipple 10C may be calibrated such that the output signal can be correlated to the applied tongue force TF. The instrumented nipple 10C may be used to evaluate tongue movement and/or strength during NNS, and/or may include an aperture 25 for fluid flow through to allow use of the instrumented nipple 10C for evaluating tongue movement and/or strength during NS. The instrumented nipple 10C may be used in conjunction with an evaluation apparatus 100, to provide direct measurement of the tongue force FT exerted on the instrumented nipple 10C during an evaluation sequence, which may be a sucking sequence. The direct movement measurements of the tongue force FT provided by the sensing device 30B may be used to measure and evaluate the subject's tongue strength. Optionally, measurement of pressure changes during the evaluation or sucking sequence may be made using the evaluation apparatus 100 and used in the evaluation of the subject's tongue movement, strength, and/or sucking capability.

Figure 7A:
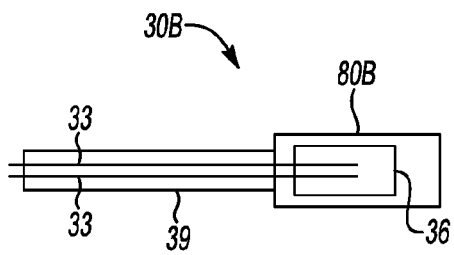
FIG. 7A is a schematic top view of an insert including the sensing device of FIG. 6A and a first example of a compliance insert.
Figure 7B:
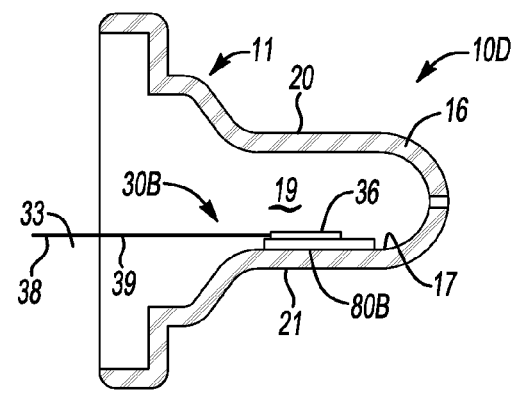
FIG. 7B is a schematic cross-sectional illustration of an instrumented nipple including the sensing device and compliance element of FIG. 7A.

As shown in FIGS. 7A and 7B, an instrumented nipple 10D may include a sensing device such as the sensing device 30B shown in FIG. 6A. The instrumented nipple 10D may further include a compliance element 80B made of deformable material which may be positioned in the nipple cavity 19 and in communication with the sensor 36. The compliance element 80B may be embedded in, adhered or affixed to the cavity wall 17, for example, using an adhesive or other means, such as bonding or molding in the compliance element 80B or otherwise positioning the compliance element 80B adjacent to or in contact with the cavity wall 17. A holder 39 may be used to position or support the compliance element 80B and sensing device 30B. The compliance element 80B may be formed of a polymeric material, a natural or synthetic rubber, or other material in any shape or orientation such that the compliance element 80B in use changes the compliance of the nipple element 11 to provide the instrumented nipple 10D. The instrumented nipple 10D may be calibrated to determine its compliance, e.g., the resistive force provided by the instrumented nipple 10D in a sucking condition. Alternatively, the characteristics of the compliance element 80B, for example the material, shape, thickness, placement, attachment method, etc., may be known and used in determining compliance. In the example shown, the compliance element 80B is configured as a polymer strip, which may be a silicone-based material, and is bonded to the cavity wall 17 of the tongue facing portion 21. The sensing device 30A includes a strain gage sensor 36 which is affixed to the compliance element 80B. In use, deformation forces applied to the nipple 10, such as tongue forces FT exerted on the instrumented nipple 10D in a sucking condition or calibration forces FC exerted on the instrumented nipple 10D during calibration, cause the compliance element 80B to systematically deform and/or move in response to the deformation forces. The deformation or strain of the compliance element 80B is detected by the sensor 36, which provides the measured strain as an output signal via leads 33. The measured strain of the compliance element 80B in a resting condition and a deformed condition such as a sucking condition may be calibrated such that the instrumented nipple 10D may be used as a noninvasive means for direct measurement of the deformation force exerted on the nipple, which may be the tongue force of a subject deforming the nipple 10D during a sucking event, and for evaluation of the subject's tongue movement and strength. Changing the compliance of the instrumented nipple 10D using the compliance element 80B changes the tongue force FT required to deform the nipple 10D in a sucking condition. By knowing the compliance of the instrumented nipple 10D including the compliance element 80B, through calibration or based on the characteristics of the compliance element 80B, the instrumented nipple 10D may be used in the intervention method 110 shown in FIG. 14, to evaluate, exercise and strengthen the subject's tongue.

Figure 8A:
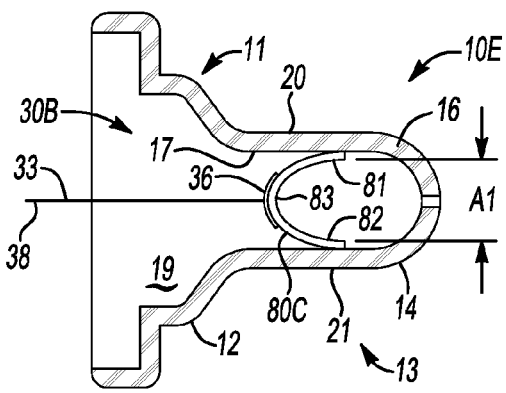
FIG. 8A is a schematic cross-sectional illustration of another example of an instrumented nipple including an insert, the insert including a compliance element and a sensing device and shown in a resting condition.
Figure 8B:
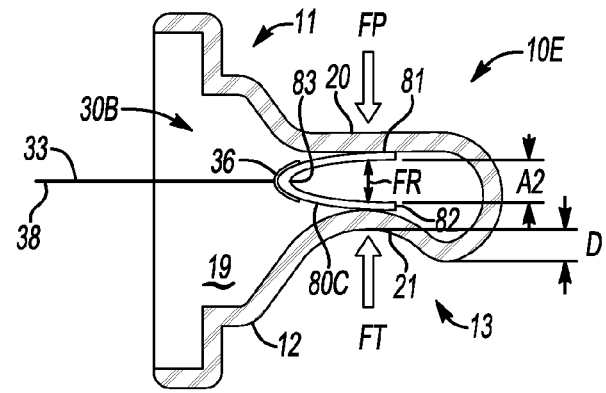
FIG. 8B is a schematic cross-sectional illustration of the instrumented nipple of FIG. 8A shown in a sucking condition.

In another example shown in FIGS. 8A and 8B, an instrumented nipple 10E may include an insert which may include a sensing device such as the sensing device 30B shown in 6A in operative communication with a compliance element 80C made of deformable material which may be positioned in the nipple cavity 19 to provide a resistive force FR to a deformation force exerted on the nipple element 11. The deformation force may be, for example, a tongue force FT applied to the instrumented nipple 10E, for example, during a sucking event, or may be a calibration force FC applied to the instrumented nipple 10E during calibration. In the example shown, the compliance element 80C is configured as a generally C-shaped element and a resting dimension A1 is the distance between the ends 81, 82 of the compliance element 80C in the resting condition shown in FIG. 8A. The compliance element 80C may be formed of a polymeric material, a natural or synthetic rubber, or other material in any shape or orientation such that the compliance element 80C inserted into the nipple cavity 19 in use changes the compliance of the nipple element 11 to provide an instrumented nipple 10E. The sensor 36, which may be configured as a strain gage, is in operative communication with an intermediate portion 83 of the compliance element 80C. The compliance element 80C is made of a deformable material, which may be a polymer based material such as silicone. The compliance element 80C may be positioned relative to, adhered or affixed to the cavity wall 17 so as to deliver a resistive force FR to the instrumented nipple 10E. The instrumented nipple 10E is shown in a resting condition in FIG. 8A and in a deformed, or sucking condition in FIG. 8B. In the resting condition, the compliance element 80C is configured to define a resting dimension A1 which corresponds to a resting strain which may be output as a resting strain signal by the sensor 36 through the leads 33.

As shown in FIG. 8B, during deformation of the instrumented nipple 10E, for example, by a tongue force FT, the nipple element 11 is deformed and the nipple wall 16 compresses the compliance element 80C such that the intermediate portion 83 is deformed and strained. The sensor 36 gauges the material strain of the compliance element 80C during deformation and outputs the strain as a measurable signal. During deformation, the ends 81, 82 are compressed together to define a deformation dimension A2 which is proportional to the deformation depth D and the strain of the intermediate portion 83. The instrumented nipple 10E may be calibrated such that the deformation force FT and the deformation distance D corresponding to the strain measurement may be determined. The compliance element 80C may be configured to provide a resistive force which is known based on characteristics of the compliance element 80C which may include material, shape, dimensions, etc, or which may be determined by calibration, such that the instrumented nipple 10E may have a known compliance. The deformation or strain of the compliance element 80C is detected by the sensor 36, which provides an output signal via leads 33, thereby providing a means for direct measurement of the deformation force exerted on the nipple 10E, which may be the tongue force FT of a subject deforming the nipple 10E, for example, during a sucking event or other tongue movement evaluation event. The movement measurements provided by the output signals of the sensing device 30B may be used in evaluation of the subject's tongue movement and strength. Changing the compliance of the instrumented nipple 10E using the compliance element 80C changes the tongue force FT required to deform the nipple 10E in a sucking condition. By knowing the compliance of the instrumented nipple 10E including the compliance element 80C, the instrumented nipple 10E may be used in the intervention method 110 shown in FIG. 14, to evaluate, exercise and strengthen the subject's tongue. The example of a compressible compliance element 80C is not intended to be limiting, and other configurations may be possible. For example, the compliance element may be generally ring shaped.

Figure 9A:
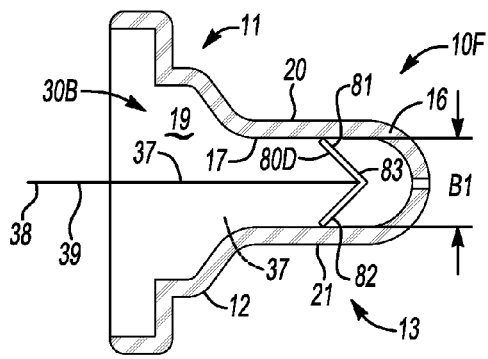
FIG. 9A is a schematic cross-sectional illustration of another example of an instrumented nipple including an insert, the insert including a non-integral compliance element and an intermediate device and shown in a resting condition.
Figure 9B:
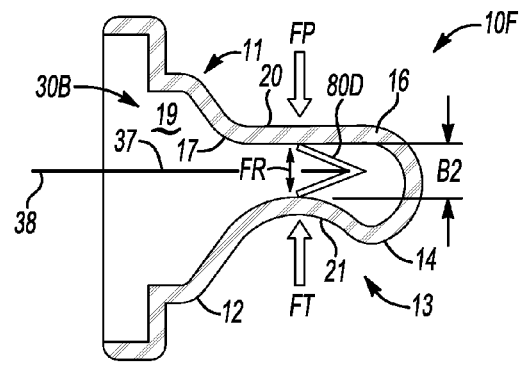
FIG. 9B is a schematic cross-sectional illustration of the instrumented nipple of FIG. 9A shown in a sucking condition.

In another example shown in FIGS. 9A and 9B, a compressible compliance element 80D is shown in operative communication with an intermediate device 37, such that the compliance element 80D and intermediate device 37 may be inserted into the nipple element 11 to provide an instrumented nipple 10F. In the example shown, the compliance element 80D is configured as a generally V-shaped insert where a resting dimension B1 is the distance between the ends 81, 82 of the compliance element 80D in the resting condition shown in FIG. 9A. The compliance element 80D may be formed of a deformable material which may be a polymeric material, a natural or synthetic rubber, a metallic material or other material or combination of materials in a shape or orientation such that the compliance element 80D inserted into the nipple cavity 19 in use changes the compliance of the nipple element 11 to provide an instrumented nipple 10F. The compliance element 80D may be positioned relative to, adhered or affixed to the cavity wall 17 so as to deliver a resistive force FR to the instrumented nipple 10F. The instrumented nipple 10F is shown in a resting condition in FIG. 9A and in a deformed, or sucking condition in FIG. 9B. In the resting condition, the compliance element 80D is configured to define a resting dimension B1 which corresponds to a resting state of the intermediate device 37. As shown in FIG. 9B, during deformation of the instrumented nipple 10F, for example, by a tongue force FT, the nipple element 11 is deformed and the nipple wall 16 compresses the compliance element 80D such that the intermediate portion 83 is deformed and strained. During deformation, the ends 81, 82 are compressed together to define a deformation dimension B2 which is proportional to the deformation depth D and the strain of the intermediate portion 83.

The intermediate device 37 is in operative communication with an intermediate portion 83 of the compliance element 80D, and may be configured to transfer or transmit a change in the compliance element 80D during deformation of the nipple 11 by a deforming force such as a tongue force FT. The change in the compliance element 80D, which may be referred to herein as a deformation change, may be in the example shown in FIGS. 9A and 9B, a change in material strain, a change in the deformed position of the intermediate portion 83 relative to the resting condition of the intermediate portion 83, or a stress imposed by movement of the compliance element 80D on the intermediate device 83. The intermediate device 37 may be configured, for example, as a triggering device, a connector, a mechanical pulley or cam system, an electrical, pneumatic, magnetic, hydraulic or optical switch, sensor, cantilever, or actuator, and the deformation change may be the response of the intermediate device 37 to deformation of the nipple element 11. The deformation change may be measurable as a force, displacement, magnetic property, pressure, optical characteristic, etc. as defined by the configuration of the intermediate device 37. In one example, the intermediate device 37 may be configured as a cantilever positioned relative to the nipple element 11 such that the cantilevered intermediate device 37 may be displaced by deformation of the nipple element 11. A sensing device 30, which may include, for example, a linear displacement sensor, may be in communication with the cantilevered intermediate device 37 to sense the displacement (deformation change) of the cantilevered intermediate device 37 and provide an output in response to the displacement (deformation change). In one example, the intermediate device 37 may include a piezoelectric material configured to sense deformation changes in the compliance element 80D. The intermediate device may be in communication with a sensing device 30 or data collector/analyzer 59, such that the intermediate device may be actuated by the deformation change of the compliance element 80D to transmit or transfer the deformation change to the sensing device 30 or data collector/analyzer 59 as an output, where the output may be in the form of an electrical, magnetic, sound, optical, or pneumatic signal, a displacing force, stress or strain provided as an input to the receiving sensor 36, sensing device 30 or data collector/analyzer 59.

The instrumented nipple 10F may be calibrated such that the output provided by the intermediate device 37 in response deformation of the compliance element 80D by a known deformation force FT may be determined. The compliance element 80D may be configured to provide a resistive force FR which is known based on characteristics of the compliance element 80D which may include material, shape, dimensions, etc, or which may be determined by calibration, such that the instrumented nipple 10F may have a known compliance. The deformation of the compliance element 80D is transmitted via the intermediate device 37 to, for example, a sensing device 30, thereby providing a means for direct measurement of the deformation force exerted on the nipple 10F and/or evaluation of a subject's tongue movement and/or strength when the deformation force exerted on the nipple is the tongue force FT exerted on the nipple 10F by the subject.

The example shown in FIGS. 9A and 9B is non-limiting, and other configurations of an instrumented nipple 10 including a compliance element 80 and intermediate device 37 are possible. For example, an intermediate device 37 configured as a non-contact optical sensor may be used in combination with the compliance element 80C shown in FIGS. 8A and 8B, where the intermediate device 37 is configured to optically sense the deformation distance A and to provide a signal corresponding to the measured deformation distance A to a data collector 59 in communication with the intermediate device 37.

Figure 10A:
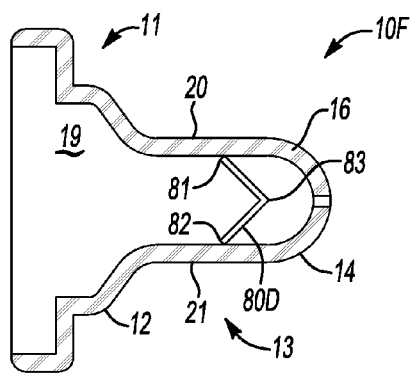
FIG. 10A is a schematic cross-sectional illustration of another example of an instrumented nipple including an insert configured as a compliance and sensing insert and shown in a resting condition.
Figure 10B:
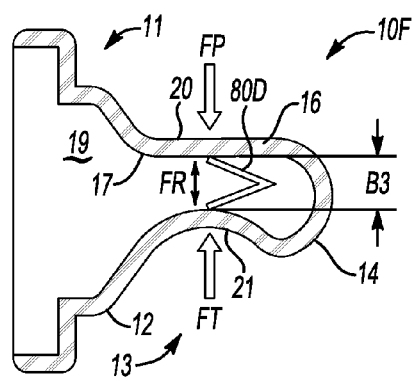
FIG. 10B is a schematic cross-sectional illustration of the instrumented nipple of FIG. 10A shown in a sucking condition.
Figure 10C:
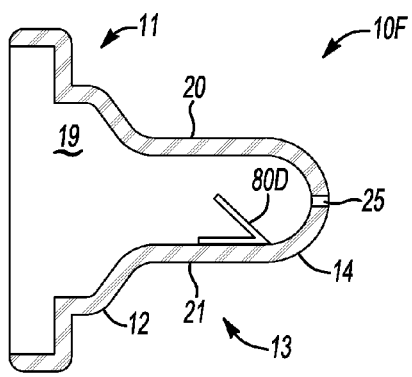
FIG. 10C is a schematic cross-sectional illustration of the instrumented nipple of FIG. 10A shown in a resting condition with the compliance and sensing insert in a permanently deformed state.

Referring now to FIGS. 10A-10C, the compliance element 80D may be configured to plastically deform at a predetermined force, to provide a visual indicator that a deformation force exceeding a predetermined force threshold has been exerted on the instrumented nipple 10F, thus allowing noninvasive evaluation of the deformation force exerted on the nipple without using an additional sensing device 30. Referring now to FIG. 10A, shown is a compliance element 80D in a resting condition in the nipple cavity 19. The compliance element 80D may be configured as described for FIGS. 9A and 9B, and may be characterized by a predetermined elastic limit, such that when the compliance element 80D is subjected to a compressive deformation force FT exceeding the predetermined elastic limit, which may correspond to compression of the compliance element 80D to a plastic deformation distance B3, the compliance element 80D undergoes plastic deformation such that upon cessation of or reduction of the deformation force below the plastic limit, the compliance element 80D remains permanently deformed and does not return to the resting deformation state defined by the resting dimension B1. In the example shown in FIG. 10C, the permanently deformed compliance element 80D may separate from the cavity wall 17 to provide a visual indicator that the predetermined elastic limit has been exceeded. The plastically deformed compliance element 80D may be measured to determine the deformation dimension B3, where the amount of plastic deformation corresponding to the deformation dimension B3 may be calibrated to indicate the maximum deformation force exerted on the instrumented nipple 10F and compliance element 80D. The example illustrated by FIGS. 10A-10C is intended to be non-limiting, and the compliance element 80 may be configured to provide other visually discernible indications, such as changes in color, texture or shape, that a predetermined force limit has been exceeded by the deformation force, such that the compliance element 80 may additionally function as a sensing device 30.

Figure 11A:
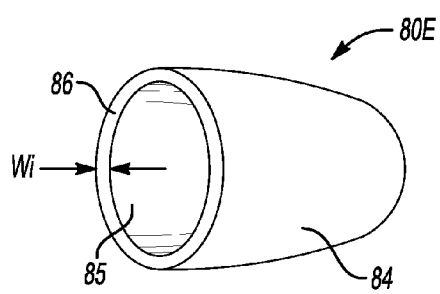
FIG. 11A is a schematic perspective illustration of another example of a compliance element.

FIGS. 11A-11C show another example of an instrumented nipple 10G including a compliance element 80E. The generally conical compliance element 80E is configured such that the outer surface 84 of the compliance element 80E substantially conforms to a circumferential portion of the inner surface 17 of the nipple cavity 19 when inserted into the nipple element 11 having a nipple wall thickness Wn, to provide an instrumented nipple 10G characterized by a resistive force FR. The compliance element 80E includes an insert cavity 85 defined by the insert wall 86, wherein the insert wall may be characterized by an insert thickness Wi. The compliance of the instrumented nipple 10G is a function of the compliance element 80E and compliance of the nipple element 11, which in combination provide a compliance proportional to the total wall thickness Wt≅Wn+Wi. The total wall thickness Wt may also be referred to as the effective wall thickness of the instrumented nipple 10. The compliance of the instrumented nipple 10G may be established by calibration using a calibration apparatus such as the calibration apparatus 60 shown in FIG. 3A, or may be determined based on the known characteristics of the nipple element 11 and compliance element 80E. The compliance element 80E may be formed of a deformable material, which may be a polymer based material such as a silicone. The compliance element 80E may be removably positioned in the cavity 19, or may be adhered or otherwise affixed to the cavity surface 17 or nipple wall 16. The compliance element 80E may include an aperture 87, such that the instrumented nipple 10G may be used for NS and NNS configurations. It would be understood that a series of compliance elements 80E having increasing wall thicknesses Wi1, Wi2 ... Win may be used in sequence, in conjunction with the evaluation and intervention method 110 shown in FIG. 14 to exercise and increase a subject's tongue strength.

FIGS. 12A and 12B show an example configuration of an instrumented nipple 10H including a compliance element 80F. The semi-conical or partially conical compliance element 80F is configured such that the outer surface 84 of the compliance element 80F substantially conforms to the tongue facing portion 21 of the nipple cavity 19 when inserted into the nipple element 11 having a nipple wall thickness Wn, to provide an instrumented nipple 10H characterized by a resistive force FR. The compliance element 80F includes an insert cavity 85 defined by the insert wall 86, wherein the insert wall may be characterized by an insert thickness Wi. The compliance of the instrumented nipple 10H is a function of the compliance element 80F and compliance of the nipple element 11, which in combination provide a compliance proportional to the total wall thickness Wt≅Wn+Wi, where Wt is the effective wall thickness of the instrumented nipple 10H. The compliance of the instrumented nipple 10H may be established by calibration using a calibration apparatus such as the calibration apparatus 60 shown in FIG. 3A, or may be determined based on the known characteristics of the nipple element 11 and compliance element 80F. The element 80F may be formed of a deformable material, which may be a polymer based material such as a silicone, a natural or synthetic rubber, etc. The compliance element 80F may be removably positioned in the cavity 19, or may be adhered or otherwise affixed to the cavity surface 17 or nipple wall 16. The compliance element 80F may be configured and/or positioned in the nipple cavity 19 such that flow of fluid through the nipple aperture 25 is not restricted, and such that the instrumented nipple 10H may be used for NS and NNS configurations. It would be understood that a series of compliance elements 80F having increasing wall thicknesses Wi1, Wi2 ... Win may be used in sequence, in conjunction with the evaluation and intervention method 110 shown in FIG. 14 to exercise and increase a subject's tongue strength.

Other combinations and configurations of instrumented nipples 10 are possible. For example, a sensing device 30 and/or intermediate device 37 may be included in each of the instrumented nipples 10F, 10G, 10H to enable direct measurement of deformation of the instrumented nipple 10 and/or compliance element 80, which may be, as described previously, a measurement of strain, displacement, or other quantifiable characteristic of the deforming compliance element 80. An instrumented nipple 10, may, by way of non-limiting example, be configured as an instrumented nipple 10A ... 10H described herein, or otherwise configured within the scope of the descriptions provided herein, and may be used in conjunction with an evaluation apparatus 100 and/or evaluation system 105, for the measurement, evaluation and/or improvement of a subject's tongue movement and/or strength. Optionally, measurement of changes in pressure during NS and/or NNS using the evaluation apparatus 100 and/or the evaluation system 105 may be performed, and the pressure data collected and included in the analysis and evaluation of tongue movement and/or strength.

Referring now to FIGS. 13A-13C, shown is a schematic illustration of a tongue movement evaluation apparatus 100D including a coupling device 90 and an instrumented nipple 10 or nipple element 11. The instrumented nipple 10 includes at least one of a sensing device 30 in communication with a compliance element 80. In one example, the coupling device 90 may include a sensing device 30, for example, an optical sensing device, configured to measure deformation of the nipple element 11. In another example, the coupling device may include a sensing device 30 in communication with a compliance element 80 via an intermediate device 37. In the example shown, the coupling device 90 is configured at a first end 91 to interface with a bottle 40. The bottle 40 may be a commercially available, e.g., standard, infant feeding bottle (baby bottle), or may be a bottle 40 configured as shown in and described for FIGS. 2A and 2B. In one example, the first end 91 may define a plurality of threads for engaging the threaded end 42 (see FIG. 2A) of the bottle 40, to create a sealed interface between the bottle 40 and coupling device 90. The example provided herein is not limiting, and other configurations of the first end 91 may be used to create a sealed interface between a container or bottle 40 and the coupling device 90. For example, the first end 91 may be configured to snap on, clip to, or create an interference fit with the container 40 to provide a sealed interface.

The coupling device 90 is configured at a second end 92 to interface with a collar 28. The collar 28 may be, in the example shown, a standard infant bottle collar or ring threadable onto the end portion 42 to retain the instrumented nipple 10 in sealing contact with the coupling device 90. In one example, the second end 92 may define a plurality of threads for engaging the collar 28, where the plurality of threads may be configured substantially similar to the plurality of threads of a standard infant feeding bottle. The coupling device 90, thus configured, is readily attachable to a standard, e.g., commercially available, infant feeding bottle 40 and bottle collar 28. As shown in FIG. 13B, the first end 92 of the coupling device 90 may define a cavity 94 of sufficient depth to receive a nipple element 11 including an extension 27. In a non-limiting example, the nipple element 11 including the extension 27 may be configured as a standard, e.g., commercially available pacifier, such as a Soothie® pacifier, such that the evaluation apparatus 100D may be assembled using the coupling device 90, an insert which may be at least one of a sensing device 30 and a compliance element 80, and a commercially available bottle 40, collar 28 and nipple element 11, which may be a standard pacifier to provide a NNS configuration, or standard feeding nipple to provide a NS or NNS configuration. In a NS configuration, fluid may be flowed from a bottle 40 connected to the first end 91 of the coupling 90 through a cavity 97 defined by an inner wall 95 of the coupling 90, through an end cavity 94 defined by the second end 92 of the coupling 90, and through an aperture 25 of the nipple element 11. The example provided herein is not limiting, and other configurations of the second end 92 may be used to position the nipple element 11 relative to the coupling device 90 and/or to retain the nipple element 11 in sealing contact with the coupling device 90. For example, the second end 92 may be configured with a recessed portion or groove into which the flange 15 of the nipple element 11 may be inserted or retained. The nipple element 11 may be configured to be extended over the second end 92 to create an interference fit with the coupling device 90 to provide a sealed interface without requiring the collar 28. The collar 28 may be configured to snap or clip onto the second end 92 or to otherwise be retained by the second end 92.

In a NNS configuration, the evaluation apparatus 100D may be used without a bottle 40. A plug 98 (see FIG. 13C) may be provided to enclose the first end 91 of the coupling device when used without a bottle 40, to protect the threaded interface, prevent contamination of or damage to the interior cavities 94, 97 of the coupling device 91, the receiver 96 or other components such as a sensing device 30, etc. housed therein. The plug 98 may be configured to sealably attach to the first end 91, to provide a sealed chamber defined by the plug 98, inner wall 95 of the coupling device 90, and nipple wall 16.

As shown in FIGS. 13A-13B, the coupling device 90 may be in communications with a sensing device 30, an intermediate device 37, and/or a receiver 96 to receive and transmit data and/or sensor signals to, for example, the data collector/analyzer 59 or a portable data storage device (not shown) such as a SIM card, flash drive, etc. which may include RAM or flash memory and be used to transfer the collected data to the data collector/analyzer 59. The communications interface 35 may be configured to transmit output signals from a sensing device 30 or intermediate device 37 included in the evaluation apparatus 100D or received via the receiver 96 of the coupling device 90. In one example, the communications interface 35 may be configured for wireless transmission of the sensor signals to the data collector/analyzer 59 using any suitable means of wireless transmission such as Bluetooth®, RFID, Wi-Fi, ZigBee® or other wireless methods.

The coupling device 90 may include a user interface 75, which may include a display and/or input/output interface for visually, audibly, or textually communicating data, analysis results, messages, instructions, alerts, etc. The coupling device 90 may include a transducer 76, which may be configured, for example, to convert an input signal received from a sensing device 30, intermediate device 37, pressure sensor 79, into an output signal to be provided to the communications interface 35, stored in a memory 78, displayed via the user interface 75, etc. The input signal may be an electrical, mechanical (force, stress, strain), electromagnetic, optical, chemical, pressure, or acoustic signal which may be converted by the transducer 76 into an output signal which may be, in a non-limiting example, an electrical, visual or audible signal. The coupling device 90 may include a power source 77, which may be a battery or power input interface, and a memory 78 configured as one or more of Read Only Memory (ROM), Random Access Memory (RAM), electrically-erasable programmable read only memory (EEPROM), etc., of a size and speed sufficient for executing the functions performed by the coupling device 90.

The coupling device 90 may include a receiver 96 which may be configured to position, connect to, and or receive a sensing device 30, intermediate device 37 or holder 39. The receiver 96 may be in operative communication with one or more of the communications interface 35, the user interface 75, the transducer 76 and the memory 78 and may be configured to transmit data and/or signals between the sensing device 30 or intermediate device 37 and one or more of these. The sensing device 30 may be integrated into the receiver 96 and/or coupling 90 as shown in FIG. 13B, and output signals may be received from a compliance element 80 via an intermediate device 37 in communication with the compliance element 80 and the integrated sensing device 30.

The coupling device 90 may optionally include a pressure gauge 79 in communication with one of the cavities 94, 97 defined by the coupling 90. A sealed chamber may be formed by the bottle cavity 41, coupling cavities 97, 94 and nipple cavity 19, such that the pressure gauge 79 in communication with the sealed chamber thus formed by the connected cavities 19, 41, 94, 97 can be used to measure pressure changes in the sealed chamber resultant from tongue movement of a subject, for example, during a sucking event, and the pressure measurements used in evaluating the tongue movement and/or tongue strength of the subject. Alternatively, the plug 98 may be sealably attached to the first end 91 of the coupling device 90 to form a sealed chamber defined by the cavities 19, 94 and 97 to measure pressure changes in the sealed chamber thus formed using the pressure gauge 79.

The tongue movement evaluation apparatus 100D including the coupling device 90 may be assembled in various configurations and combinations of sensing devices 30, compliance elements 80, intermediate devices 37, etc., including but not limited to the configurations shown in FIGS. 13A-13C. Referring to FIG. 13B, the evaluation apparatus 100D includes a nipple element 11 configured as a pacifier which is positioned in sealing contact with the second end 92 of the coupling 90, and retained in position by the collar 28, to provide a NNS configuration. In a NNS configuration, a bottle 40 or plug 98 may be optionally attached to the first end 91. Alternatively, a feeding nipple element 11 including an aperture 25 may be substituted for the pacifier nipple element to provide a NS configuration. In the NS configuration, a bottle 40 containing a fluid 24 may be attached as shown in FIG. 13A. A compliance element generally indicated at 80 is positioned in the nipple cavity 19 to provide an instrumented nipple 10. The compliance element 80 may be, by way of non-limiting example, configured as a compliance element 80A, 80B, 80C or 80D. The coupling device 90 includes an integrated sensing device 30 for receiving signals from the compliance element 80 via an intermediate device 37 which is in operative communications with the compliance element 80 and the integrated sensing device 30. In one example, the intermediate device 37 may be connected to the integrated sensing device 30 via the receiver 96.

A holder 39 may be provided to support or position the intermediate device 37 and/or the compliance element 80 with respect to the nipple element 11 and the receiver 96. The receiver 96 may be configured to receive the holder 39 in an oriented position relative to the nipple element 11, and/or a tongue facing portion 21 of the nipple element 11. The compliance element 80 may be oriented or positioned to be deformed by and/or sense a deformation force exerted on the nipple element 11. The deformation force may be a tongue force FT exerted on the tongue facing portion 21 of the instrumented nipple 10 by a subject during a sucking session, such that noninvasive direct measurement of the deformation force may be made using the evaluation apparatus 100D to evaluate the tongue movement, tongue strength and/or sucking capability of the subject.

In another example configuration shown in FIG. 13C, the evaluation apparatus 100D may include a sensing device 30B and compliance element 80B which is inserted into the nipple element 11 to provide an instrumented nipple 10. The sensing device 30B may include a strain gage sensor 36 operatively attached to the compliance element 80B to measure strain of the compliance element 80B during deformation of the nipple element 11. The leads 33 attached to the strain gage sensor 36 may be operatively attached to the receiver 96 to provide strain data via the receiver 96 to the memory 78, user interface 75 and/or communications interface 35. The sensing device 30, or a portion thereof such as the leads 33, may optionally be positioned or fixtured using a holder 39. The receiver 96 may be adapted to receive the holder 39 and the leads 33.

The coupling device 90 may include a plurality of receivers 96 in communication with the communication interface 35, such that more than one sensing device 30, compliance element 80, and/or intermediate device 37 may be included in the evaluation apparatus 100D, for example, when it may be desirable to measure the deformation force in more than one location within the nipple element 11.

In use, an evaluation apparatus kit (not shown) may be provided including the coupling device 90 and one or more inserts consisting of at least one of a sensing device 30 and compliance element 80. The kit may include a plurality of compliance elements 80, each having a different known compliance, for use with the intervention method 110 shown in FIG. 14. The kit elements, e.g., the coupling device 90 and insert may be combined with a standard nipple element 11 and/or bottle 40 to provide an evaluation apparatus 100D. The kit and/or the some or all of the kit elements may be provided in a sterilized condition.

Referring now to FIG. 14, a method generally indicated at 110 is illustrated for the evaluation of tongue movement and/or tongue strength of a subject using an evaluation apparatus 100 and for providing an intervention to increase the tongue strength of the subject using one or more instrumented nipples 10 to exercise the subject's tongue. The compliance and resistive force of the instrumented nipple 10 may be selected or configured based on the measured tongue movement and/or strength of the subject, and a series of instrumented nipples 10 of differing compliance may be used in the intervention method and presented to the subject in order of decreasing compliance using the instrumented nipple 10 as a pacifier (NNS) or feeding bottle nipple (NS) to strengthen the tongue muscle, e.g., increase the tongue force exerted by the subject. Similar to exercising any muscle of the body, the tongue can be strengthened through resistance training Resistive force FR can be applied to the tongue via the instrumented nipple 10 during sucking Instrumented nipples 10 of increasing (stiffer) compliance can be introduced in subsequent evaluation sequences (pacifier or feeding sessions) as the tongue muscles progress and become stronger.

In a first step 111 of the method 110, an initial sucking session is conducted with a subject using an evaluation apparatus 100 which may include a nipple 10 of known compliance and/or a sensing device 30. The subject may be a preterm infant. The evaluation apparatus 100 may be configured as described herein such that noninvasive direct measurement of the deformation force, e.g., the tongue force FT exerted by the subject on the nipple element 11 of the evaluation apparatus 100 is obtained. The tongue force FT may be measured at specific points during a sucking cycle, using an initial insert including a sensing device 30, for example, and/or a compliance element 80 configured to provide an initial resistive force. Other measurements collected during the first step 111 may include the amount of sucking cycles completed and/or volume of fluid expelled from the nipple 10 during the feeding session.

At a second step 112, the tongue movement and/or tongue strength of the subject is evaluated using the data monitored or collected during step 111. Evaluation of tongue movement and/or tongue strength may include analysis of the force pattern during the evaluation sequence, which may be a sucking sequence, measurement of deformation of the nipple element, frequency and rate change analysis, calculation of strength parameters such as power, impulse and work, etc. For example, the amount of sucking (deformation) cycles completed and/or volume of fluid expelled from the nipple 10 during the feeding session of step 111 may be used to calculate the amount of work performed by the subject's tongue during the feeding session. Measurements of the tongue force FT at specific points during the sucking or deformation cycle may be used to calculate impulse and power capabilities of the subject's tongue. Sucking frequency and rate, and/or the rate of force development over the sucking or evaluation sequence may be analyzed to evaluate fatigue or stamina.

At step 113, a comparison of the subject's strength level determined at step 112 to a tongue movement objective established for the subject is made. If the tongue movement objective has been met, the method continues to step 114, and rehabilitation and/or intervention is completed. Optionally, the intervention may continue even though the tongue movement objective has been met, by returning from step 114 to step 111 periodically to conduct an evaluation session to monitor whether the subject's tongue movement capability has been maintained, e.g., continues to meet the objective. If, at step 112 it is determined that the subject has not met the tongue movement objective, the method continues to step 115, where the evaluation apparatus 100 may be modified to include an instrumented nipple 10 having less compliance than the previous instrumented nipple 10, e.g., having greater resistive force, to exercise and develop the subject's tongue movement and strength. By way of non-limiting example, the evaluation apparatus 100 and/or instrumented nipple 10 may be modified to include another insert, which may be referred to herein as a subsequent insert, which may be configured to provide a resistive force different from, and typically greater than, the insert used for the initial evaluation session. The method returns to step 111 and a subsequent evaluation session is conducted with the subject using the evaluation apparatus 100 including the instrumented nipple 10, which may include a subsequent insert having a different or decreased compliance than the initial insert. The method continues with conducting subsequent evaluation sessions and evaluating the output from the subsequent sessions until the subject has achieved the tongue movement objective or strength threshold established for the subject. A series of instrumented nipples 10 or subsequent compliance elements 30, each having increasing resistive force (decreasing compliance), may be used in conjunction with the method 100 to exercise and increase the strength of the subject's tongue during subsequent evaluation sessions, until the tongue movement objective and/or strength threshold is met.

The configurations of the instrumented nipple 10, sensing device 30, compliance element 80 and evaluation apparatus 100 shown in the figures are not intended to be limiting. For example, the compliance element 80 and/or sensing device 30 may be configured to measure or indicate deformation using other characteristics or methods, which may include chemical, electrical, physical, or any other material property change such as color, transparency, etc. Other methods of deformation evaluation include but are not limited to visual inspection, chemical testing, material measurement, fluid displacement, shape analysis and pressure measurement. The compliance element 80 may be configured to include non-polymeric materials, including metallic materials, composites, and multi-layer materials.

The detailed description and the drawings or figures are supportive and descriptive of the invention, but the scope of the invention is defined solely by the claims. While some of the best modes and other embodiments for carrying out the claimed invention have been described in detail, various alternative designs and embodiments exist for practicing the invention defined in the appended claims.

The invention claimed is:

1. A method comprising:
   deflecting a cantilever element of an evaluation apparatus by movement of a nipple element by a deformation force exerted on the nipple element;
   measuring, using the evaluation apparatus including the nipple element, an output generated by the deflection of the cantilever element by movement of the nipple element by the deformation force exerted on the nipple element;
   wherein:
      the evaluation apparatus includes a coupling device;
      the nipple element is removably attached to the coupling device;
      the nipple element includes an inner surface defining a nipple cavity;
      the coupling device includes a sensing device and is configured to receive the cantilever element such that the cantilever element is configured to be operatively attached only at one of:
         one side of the cantilever element to the coupling device; and
         two opposing sides of the cantilever element to the coupling device;
      such that the cantilever element is in operative communication with the sensing device, and positioned within the nipple cavity adjacent the inner surface of the nipple element and detached from the nipple element;
   wherein the cantilever element is configured to generate the output in response to deflection of the cantilever element in direct contact with the inner surface; and
   wherein the output:
      corresponds to the movement of the nipple element resultant from the deformation force exerted on the nipple element; and
      is received as input by the sensing device.

2. The method of claim 1, wherein:
   the evaluation apparatus defines a fluid chamber in communication with the nipple cavity and configured to receive a fluid,
   the nipple element includes an aperture in fluid communication with the nipple cavity such that the evaluation apparatus is configured for nutritive sucking; and
   the cantilever element is configured to be in contact with fluid in the fluid chamber and nipple cavity during nutritive sucking.

3. The method of claim 1, further comprising:
   exercising a tongue of a subject including sucking of a nipple by the subject;
   wherein the nipple exerts a resistive force resistant to movement of the tongue of the subject.

4. The method of claim 3, wherein:
   the nipple defines a nipple cavity;
   the method further comprising:
      altering the resistive force exerted by the nipple by one of:
         providing a fluid in the nipple cavity; and
         exerting a pressure on the nipple cavity.

5. The method of claim 3, further comprising:
   subsequent to exercising the tongue of the subject, measuring the output generated by the deformation force exerted on the nipple element by the subject, using the evaluation apparatus; and
   comparing the output measured prior to exercising the tongue of the subject with the output measured after exercising the tongue of the subject.

6. The method of claim 5, further comprising:
   making a clinical decision based on the comparison of the output measured before and after exercising the tongue of the subject;
   wherein the clinical decision is related to one of:
      tongue strength of the subject,
      neuromuscular integrity of the subject, and
      tongue coordination of the subject.

7. The method of claim 3, wherein:
   the nipple is one of the nipple element and another nipple;
   the nipple exerts a resistive force resistant to movement of the tongue of the subject; and
   the resistive force is defined by a compliance of the nipple.

8. The method of claim 7, further comprising:
   providing a fluid to the nipple cavity;
   wherein the compliance of the nipple is altered by one of
      a fluid viscosity of the fluid, and
      a pressure of the fluid in the nipple cavity.

9. The method of claim 1, wherein deflection of the cantilever element exerts a resistive force resistant to movement of the tongue of the subject.

10. The method of claim 1, wherein the output corresponds to movement of the nipple element.

11. The method of claim 1, wherein the deformation force is exerted on the nipple element by movement of a tongue of a subject;
   the method further comprising:
      determining a measure of tongue strength of the subject using the output.

12. The method of claim 11, wherein the measure of tongue strength is one of force, work, impulse, and fatigue.

13. The method of claim 11, further comprising
   determining a measure of neuromuscular integrity related to tongue coordination of the subject using the output.

14. The method of claim 13, wherein the measure of neuromuscular integrity is one of:
   a measure of sucking integrity coordination, wherein sucking includes one of pacifier sucking and bottle sucking;
   a measure of coordination of a suck-swallow-breathe cycle;
   a measure of feeding coordination;
   a measure of tongue strength; and
   a measure of temporal events related to tongue movement.

15. The method of claim 11, further comprising:
   determining a plurality of measures including at least one of a measure of tongue strength and a measure of neuromuscular integrity related to tongue coordination;
   wherein at least one of the plurality of measures includes at least one temporal measure; and
   determining one of:
      temporal coordination of two or more of the plurality of measures;
      variability of one or more of the plurality of measures; and
      a pattern defined by one or more of the plurality of measures.

16. The method of claim 1, wherein the output corresponds to a movement of the cantilever element.

17. The method of claim 16, wherein:
   the sensing device includes a sensor configured to measure the movement of the cantilever element; and
   the sensor is a non-contact sensor.

18. The method of claim 17, wherein the non-contact sensor is a proximity sensor.

19. The method of claim 17, wherein the non-contact sensor is one of an infrared sensor, a magnetic, an induction sensor, a capacitive sensor, a photoelectric sensor, and an optic sensor.

20. The method of claim 1, wherein the sensing device is external to the coupling device.

21. The method of claim 11, wherein the evaluation apparatus includes a sensor configured to generate a sensor output defined by the tongue movement of the subject;
the method further comprising:
sensing the tongue movement of the subject using the sensor; and
generating the sensor output from the sensor corresponding to the tongue movement of the subject.

22. The method of claim 21, further comprising:
determining one of:
tongue strength of the subject,
neuromuscular integrity of the subject, and
tongue coordination of the subject
using the output of the cantilever element in combination with the sensor output.

23. The method of claim 21, wherein the sensor includes one of a pressure sensor, a flow sensor, a fluid volume sensor, an infrared sensor, a piezoelectric sensor, a resistive sensor, an inductive sensor, a capacitive sensor, and a magnetic sensor.

24. The method of claim 11, further comprising:
non-invasive imaging of the tongue of the subject.

25. The method of claim 1, further comprising:
transmitting a signal defined by the output from the sensing device; and
one of displaying, processing, and storing the transmitted signal.

26. The method of claim 11, further comprising:
measuring the output corresponding to movement of the tongue of the subject at a plurality of timepoints over a period of time;
storing in a database the output received by the sensing device at the plurality of timepoints; and
comparing the output at the plurality of timepoints to evaluate the movement of the tongue of the subject over the period of time.

27. The method of claim 11, further comprising:
measuring the output corresponding to the movement of the tongue of each of a plurality of subjects;
storing in a database the output corresponding to each of the plurality of subjects in a database; and
comparing the output of one of the plurality of subjects to the output of another of the plurality of subjects.

28. The method of claim 1, further comprising:
calibrating a movement of the nipple element to a measure of tongue strength.

29. The method of claim 28, wherein the measure of tongue strength is one of force, work, impulse, fatigue, and a temporal derivative of at least one of force, work, impulse and fatigue.

30. The method of claim 1, further comprising:
calibrating a movement of the nipple element to a measure of neuromuscular integrity related to tongue coordination.

31. The method of claim 30, wherein the measure of neuromuscular integrity is one of:
a measure of sucking integrity coordination, wherein sucking includes one of pacifier sucking and bottle sucking;
a measure of coordination of a suck-swallow-breathe cycle;
a measure of feeding coordination;
a measure of tongue strength; and
a measure of temporal events related to tongue movement.

32. The method of claim 11, further comprising:
making a clinical decision of tongue strength using the output.

33. The method of claim 11, further comprising:
making a clinical decision of neuromuscular integrity related to tongue coordination using the output.

34. The method of claim 2, further comprising:
measuring, during nutritive sucking of the nipple element by a subject, the output generated in response to movement of the nipple element by a deformation force exerted on the nipple element by a tongue of the subject.

* * * * *